United States Patent [19]

Suzuki et al.

[11] Patent Number: 5,018,509

[45] Date of Patent: May 28, 1991

[54] ENDOSCOPE INSERTION CONTROLLING APPARATUS

[75] Inventors: Akira Suzuki; Hiroki Hibino; Hiroyuki Fukuda; Yutaka Takahashi; Akibumi Ishikawa, all of Hachioji, Japan

[73] Assignee: Olympus Optical Co., Ltd., Tokyo, Japan

[21] Appl. No.: 454,620

[22] Filed: Dec. 21, 1989

[30] Foreign Application Priority Data

| Feb. 21, 1989 | [JP] | Japan | 1-40929 |
| Feb. 21, 1989 | [JP] | Japan | 1-40932 |
| Jun. 27, 1989 | [JP] | Japan | 1-166369 |
| Oct. 16, 1989 | [JP] | Japan | 1-270119 |

[51] Int. Cl.$^5$ ............................ A61B 1/04; A61B 1/06
[52] U.S. Cl. ............................................ 128/6; 358/98
[58] Field of Search ............................. 128/6; 358/98

[56] References Cited

U.S. PATENT DOCUMENTS

| 4,176,662 | 12/1979 | Frazer | 128/6 |
| 4,902,129 | 2/1990 | Siegmund et al. | 128/6 X |
| 4,910,590 | 3/1990 | Gillies et al. | 128/6 X |
| 4,916,533 | 4/1990 | Gillies et al. | 128/6 X |

FOREIGN PATENT DOCUMENTS 61-278813 12/1986 Japan .
62-41635 2/1987 Japan .

Primary Examiner—William H. Grieb
Attorney, Agent, or Firm—Armstrong, Nikaido, Marmelstein, Kubovcik & Murray

[57] ABSTRACT

An endoscope insertion controlling apparatus includes a region extracting apparatus for extracting a plurality of regions corresponding to brightness from an endoscope image, for example, by setting a plurality of threshold levels of brightness and a judging apparatus for determining endoscope inserting conditions such as an inserting direction and progress speed based on an arrangement of the respective regions extracted by the region extracting apparatus. An endoscope inserting direction detecting apparatus includes a light receiving apparatus for receiving light from a visual field narrower than an ordinary observing field of the endoscope, a scanning apparatus for scanning the visual field of the light receiving apparatus and a judging apparatus for determining an endoscope inserting direction based on the received light amount by the light receiving apparatus in the respective visual field directions obtained by scanning the visual field of the light receiving apparatus by the scanning apparatus.

24 Claims, 17 Drawing Sheets

FIG.6
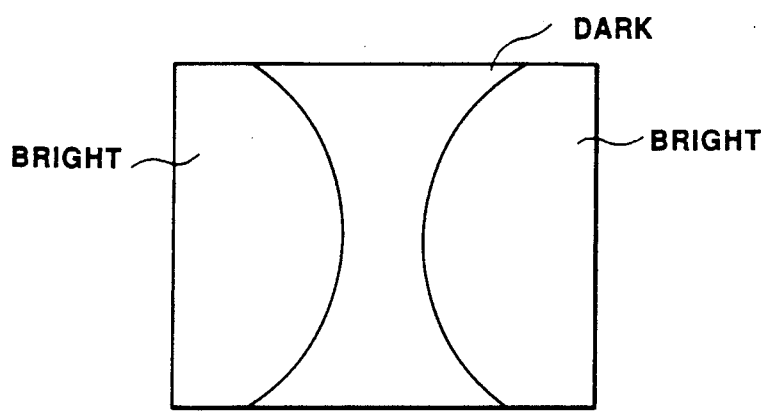
FIG.7(a)
| 1 | 1 | 1 | 1 | 1 |
|---|---|---|---|---|
| 0 | 1 | 1 | 1 | 0 |
| 0 | 1 | 1 | 1 | 0 |
| 0 | 1 | 1 | 1 | 0 |
| 1 | 1 | 1 | 1 | 1 |
FIG.7(b)
| 1 | 1 | 1 | 1 | 1 |
|---|---|---|---|---|
| 0 | 1 | 1 | 1 | 0 |
| 0 | 0 | 1 | 0 | 0 |
| 0 | 0 | 1 | 0 | 0 |
| 0 | 0 | 1 | 0 | 0 |
FIG.9
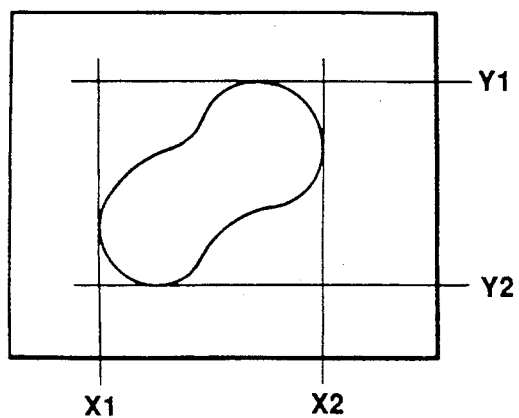

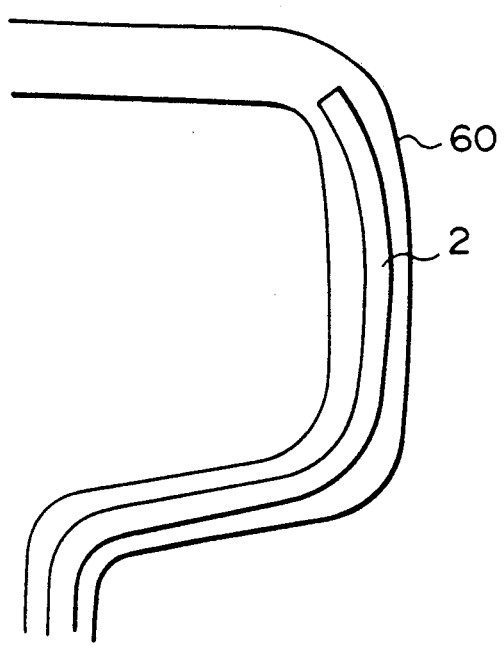
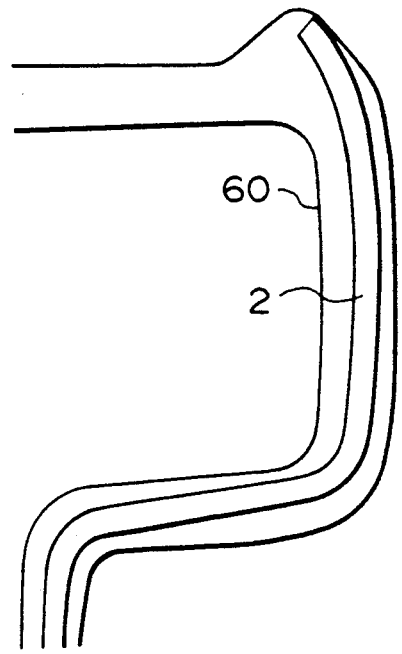
FIG.15
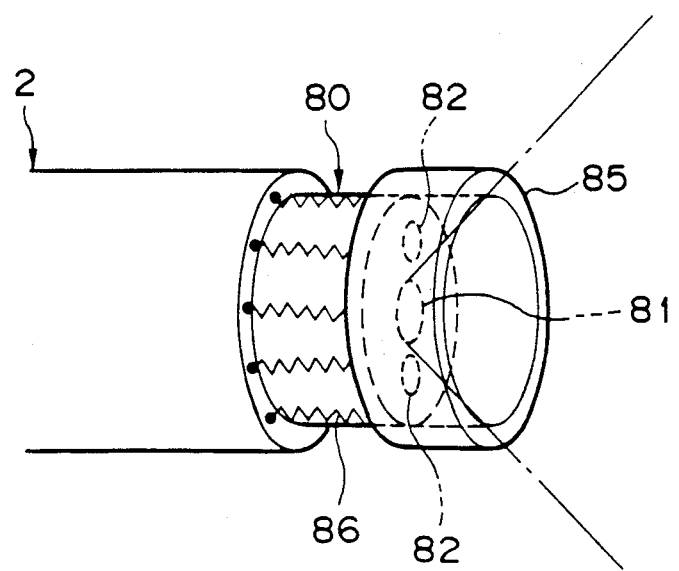

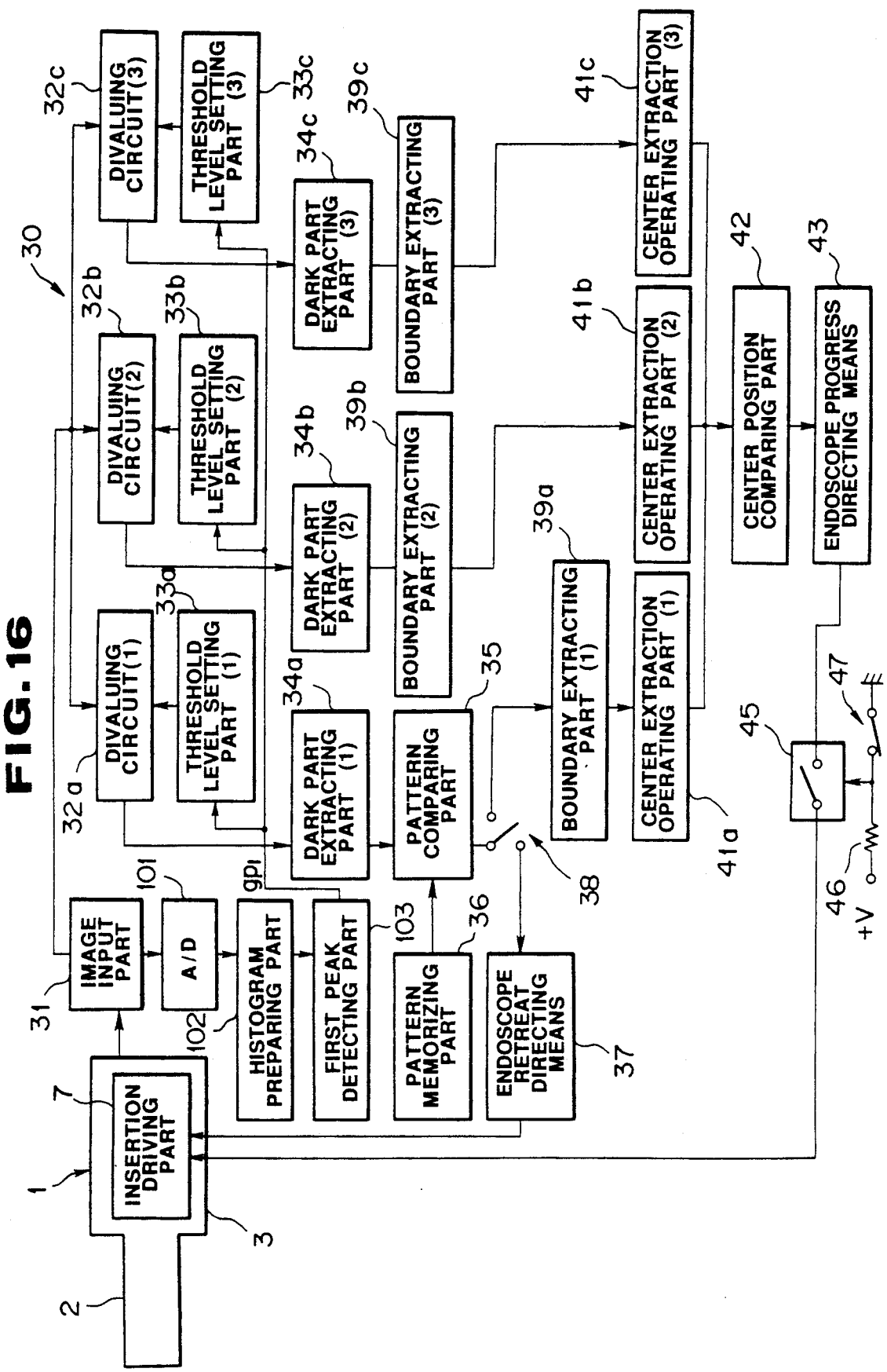

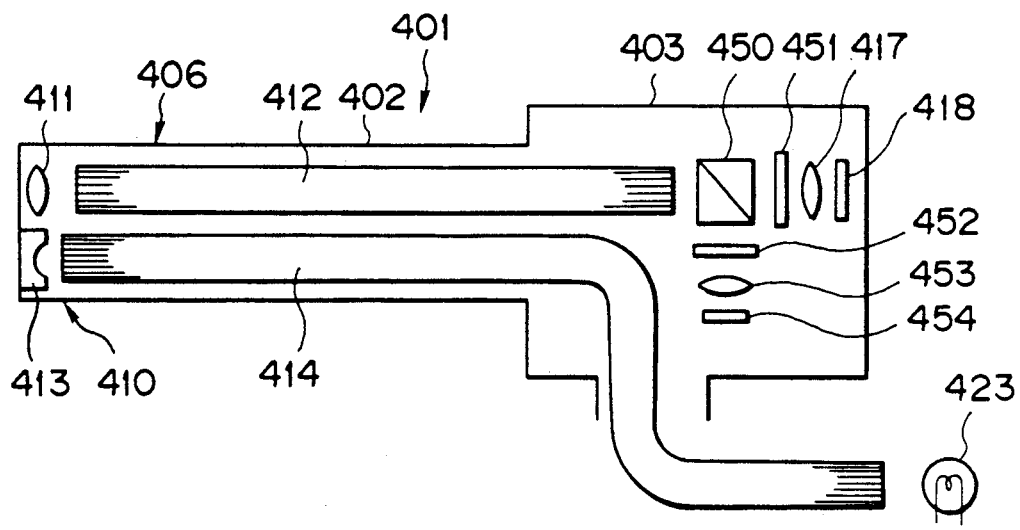
FIG. 31
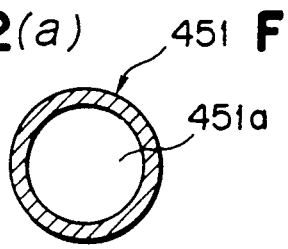
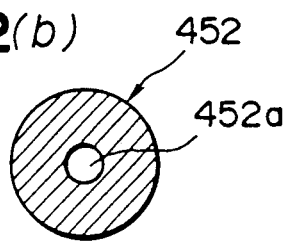
FIG. 32(a)  FIG. 32(b)
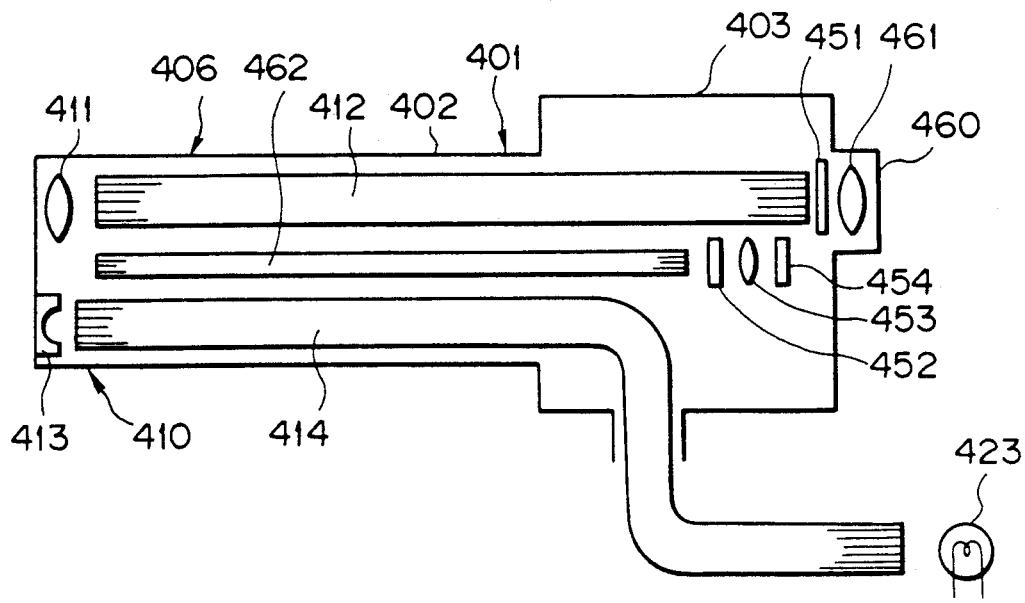
FIG. 33

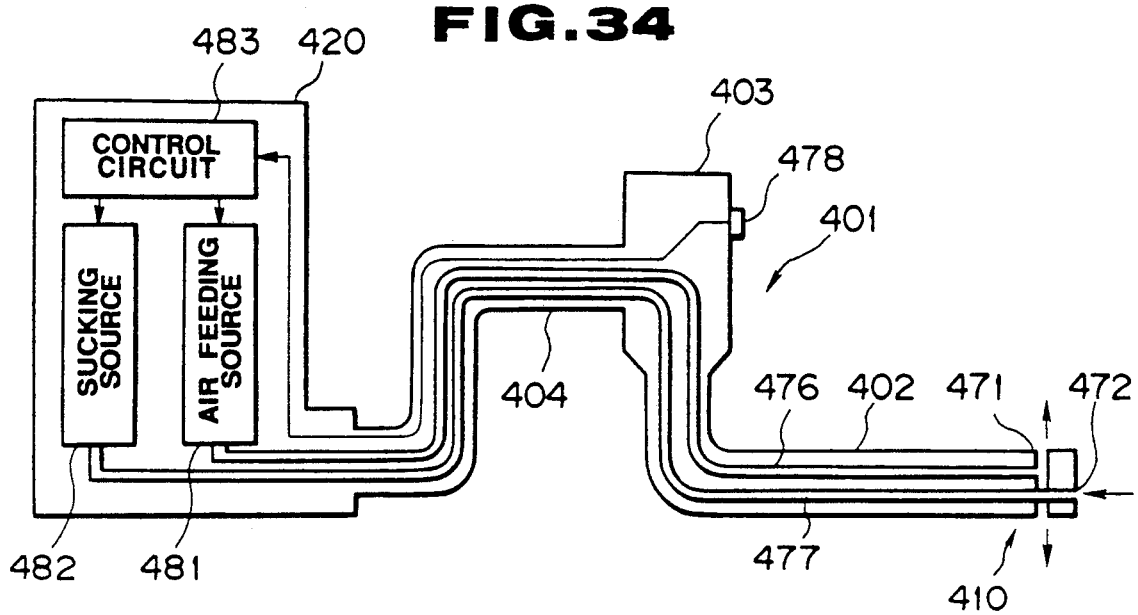
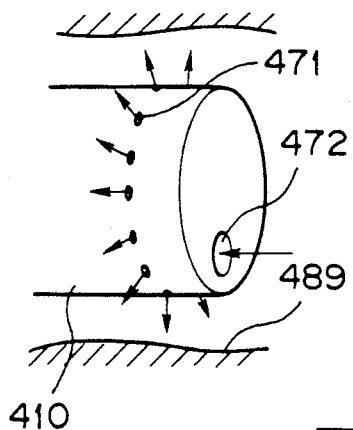
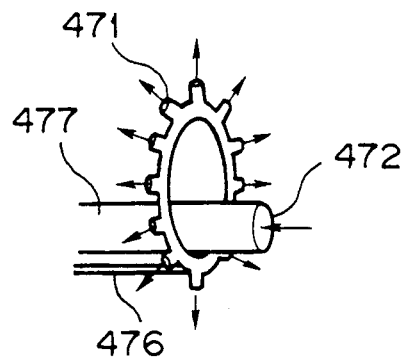
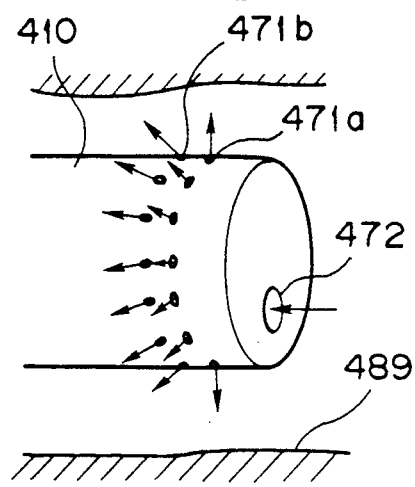

ENDOSCOPE INSERTION CONTROLLING APPARATUS

BACKGROUND OF THE INVENTION

1. Field of the Invention

This invention relates to an endoscope insertion controlling apparatus capable of determining the endoscope inserting conditions and adapted to the automatic insertion of the endoscope.

2. Related Art Statement

Recently, an endoscope, whereby organs within a body cavity can be observed by inserting an elongated insertable part into the body cavity or, as required, various therapeutic treatments can be made by using treating instruments inserted through a treating instrument channel, is extensively utilized.

In inserting an endoscope into a tube cavity or the like, conventionally, while observing the endoscope image, the operator determines the endoscope inserting direction and curves the insertable part on the tip side so as to be directed in the inserting direction.

High technique and skill have been requires to insert an endoscope in the inspection of large intestines or the like.

A technique for providing an endoscope insertable part at the tip with an oscillator to detect the position of the tip is disclosed in U.S. Pat. No. 4,176,662. However, with this technique, the endoscope inserting direction can not be detected.

Therefore, a method of detecting the endoscope inserting direction by extracting dark regions of the endoscope image is suggested in U.S. Pat. No. 4,910,590.

In case the tube cavity is linear, the endoscope insertable part may proceed straight in the detected inserting direction but, in case the tube cavity is curved, the insertable part must proceed in response to the curved state. There has been so far no means of detecting the curved state of the tube cavity or the like.

OBJECT AND SUMMARY OF THE INVENTION

An object of the present invention is to provide an endoscope insertion controlling apparatus whereby endoscope inserting conditions can be determined in response to the state of an object to be inspected and a proper insertion corresponding to the state of the object is made possible.

Another object of the present invention is to provide an endoscope inserting direction detecting apparatus whereby the endoscope inserting direction can be detected.

The endoscope insertion controlling apparatus comprises a region extracting device for extracting a plurality of regions corresponding to brightness from an endoscope image, for example, by setting a plurality of threshold levels of brightness and a judging device for determining endoscope inserting conditions such as an inserting direction and proceeding speed. The endoscope inserting direction detecting apparatus comprises a light receiving device for receiving the light from a visual field narrower than an ordinary observing visual field of the endoscope, a scanning device for scanning the above mentioned visual field of the above mentioned light receiving device and a judging device for determining an endoscope inserting direction based on the received light amount by the light receiving device in the respective visual field directions obtained by scanning the visual field of the light receiving device by the scanning device.

The other features and advantages of the present invention will become apparent with the following explanation.

BRIEF DESCRIPTION OF THE DRAWINGS

FIGS. 1 to 11 relate to the first embodiment of the present invention.

FIG. 1 is a block diagram showing the formation of an endoscope automatically inserting apparatus.

FIG. 2 is an explanatory view showing the formation of an endoscope apparatus.

FIG. 3 is a circuit diagram showing a divaluing circuit and threshold level setting part.

FIGS. 4(a) and 4(b) are explanatory diagrams of the operation of dark part extracting parts.

FIG. 5 is an explanatory view showing a plurality of regions extracted by the dark park extracting part.

FIG. 6 is an explanatory view showing an endoscope image when the endoscope tip has approached too near the object to be inspected.

FIG. 7(a) and 7(b) are explanatory views showing examples of comparative patterns of a pattern comparing part.

FIG. 8 is an explanatory view of the operation of a boundary extracting part.

FIG. 9 is an explanatory view of the operation of a center extracting operation part.

FIGS. 12(a) and 12(b) are explanatory views showing the manner of inserting the endoscope into large intestines.

FIG. 15 is a perspective view of an endoscope tip by which it can be known that the tip of the insertable part has butted against an object to be inspected.

FIGS. 16 to 19 relate to the second embodiment of the present invention.

FIG. 16 is a block diagram showing the formation of an endoscope automatically inserting apparatus.

FIG. 17 is a circuit diagram showing a divaluing circuit and threshold level setting part for setting other regions.

FIG. 18 is a circuit diagram showing a divaluing circuit and threshold level setting part for setting other regions.

FIGS. 21 to 25 relate to the fourth embodiment of the present invention.

FIG. 21 is a sectioned view of a self-running type inserting body.

FIG. 22 is a sectioned view on line A—A' in FIG. 21.

FIG. 23 is a circuit diagram showing an electrifying means for a shape memorizing alloy.

FIG. 24 is a timing chart showing the timing of electrifying the shape memorizing alloy.

FIG. 26 is an explanatory view showing the formation of an endoscope apparatus.

FIG. 27 is an explanatory view of a visual field mark.

FIG. 28 is a block diagram showing the formation of an automatic inserting apparatus.

FIG. 29 is an explanatory view showing an objective lens visual field converting means.

FIG. 30 is a flow chart for explaining the operation of this embodiment.

FIGS. 31 and 32 relate to the sixth embodiment of the present invention.

FIG. 31 is an explanatory view showing the formation of an endoscope.

FIGS. 32(a) and 32(b) are explanatory views showing masks.

FIG. 33 is an explanatory view showing the formation of an endoscope in the seventh embodiment of the present invention.

FIGS. 34 to 36 relate to examples of endoscopes in which the insertability is improved.

FIG. 34 is an explanatory view showing the formation of an endoscope apparatus.

FIG. 35 is a perspective view of a tip part.

FIG. 36 is a perspective view showing a pipe line formation in the tip part.

FIG. 37 is a perspective view of a tip part in another example of an endoscope in which the insertability is improved.

DETAILED DESCRIPTION OF THE PREFERRED EMBODIMENTS

FIGS 1 to 11 show the first embodiment of the present invention.

Figure 2:
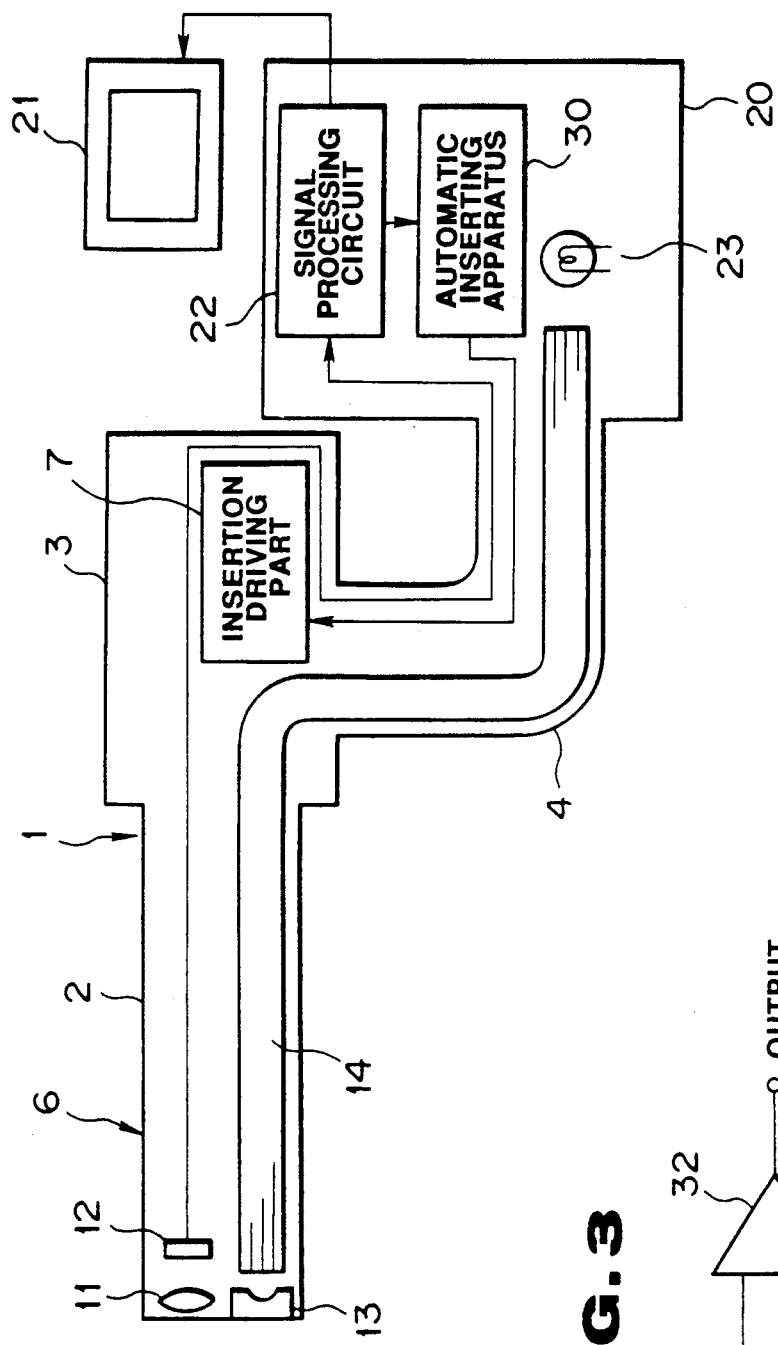

As shown in FIG. 2, an endoscope apparatus comprises an endoscope 1, a control apparatus 20 connected with this endoscope 1 and a monitor 21 connected to this control apparatus 20.

The above mentioned endoscope 1 comprises an elongate flexible insertable part 2 and an operating part 3 connected to the insertable part 2 at the rear end. A flexible universal cord 4 is extended sidewise from the above mentioned operating part 3 and is connected at the end to the above mentioned control apparatus 20.

A curvable part 6 is provided on the tip side of the above mentioned insertable part 2 and is controlled to be curved by an insertion driving part 7 provided in the endoscope 1. In order to operate the above mentioned curvable part 6 to be curved, for example, a plurality of angle wires are inserted through the insertable part 2, are fixed at the tips to the curvable part 6 on the tip side and are pulled at the rear ends by a motor provided in the above mentioned insertion driving part so that the above mentioned curvable part 6 may be curved in any direction. As a curving means, an actuator using a shape memorizing alloy or the like may be provided within the above mentioned curvable part 6.

In this embodiment, the insertable part 2 can be advanced by the above mentioned insertion driving part 7. As this insertable part 2 advancing means, for example, a means shown in the publication of Japanese patent application Laid Open No. 4,1635/1987 can be used or a means of paying out the insertable part 2 may be provided on the rear end side of the insertable part 2.

An observing window and, for example, two illuminating windows are provided in the tip part of the above mentioned insertable part 2. An objective lens 11 is provided inside the above mentioned observing window. A solid state imaging device 12 is arranged in the image forming position of this objective lens 11 and is connected to a signal processing circuit 22 provided in the above mentioned control apparatus 20 through signal lines inserted through the above mentioned insertable part 2, operating part 3 and universal cord 4. A light distributing lens 13 is provided inside the above mentioned illuminating window. A light guide 14 made of a fiber bundle is connected to this light distributing lens 13 at the rear end, is inserted through the above mentioned insertable part 2, operating part 3 and universal cord 4 and is connected at the entrance end to the above mentioned control apparatus 20. An illuminating light emitted from a light source apparatus 23 provided in this control apparatus 20 enters the above mentioned light guide 14 at the entrance end.

The above mentioned solid state imaging device 12 is driven by the above mentioned signal processing circuit 22 and the output signal of this solid state imaging device 12 is process to be a video signal by the above mentioned signal processing circuit 22. The video signal output from this signal processing circuit 22 is input into a monitor 21 in which the object image is displayed.

The endoscope 1 is not limited to be the one having the solid state imaging device 12 in the tip part of the insertable part 2 as shown in FIG. 2 but may be a fiber scope transmitting an image to an eyepiece part through an image guide made of a fiber bundle and a television camera connected to the eyepiece part of this fiber scope.

An automatic inserting apparatus 30, controlling the above mentioned insertion driving part 7 by determining the inserting conditions of the endoscope 1, is provided within the above mentioned controlling apparatus 20 into which the video signal from the above mentioned signal processing circuit 22 is input.

Figure 1:
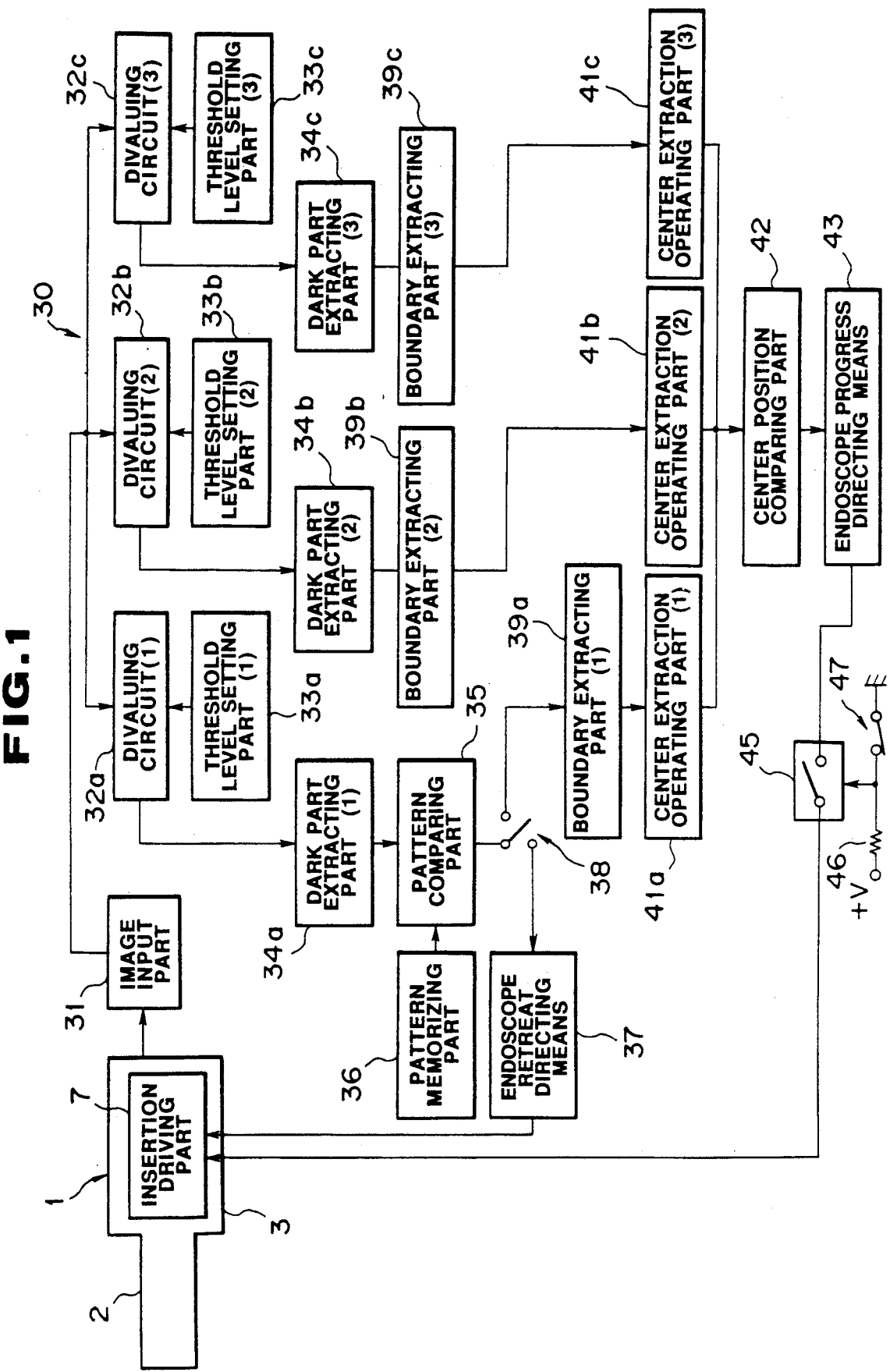

The above mentioned automatic inserting apparatus 30 shall be explained in the following with reference to FIG. 1.

The automatic inserting apparatus 30 has an image input part 31 inputting an image signal of the endoscope 1 and the image signal input from this image input part 31 is input into a plurality of, for example, three divaluing circuits (1 to 3) 32a to 32c. These respective divaluing circuits 32a to 32c convert the endoscope images to divalued images by using the threshold levels set by threshold level setting parts (1 to 3) 33a to 33c as threshold values. The respective threshold level setting parts 33a, 33b and 33c have different threshold levels.

Figure 3:
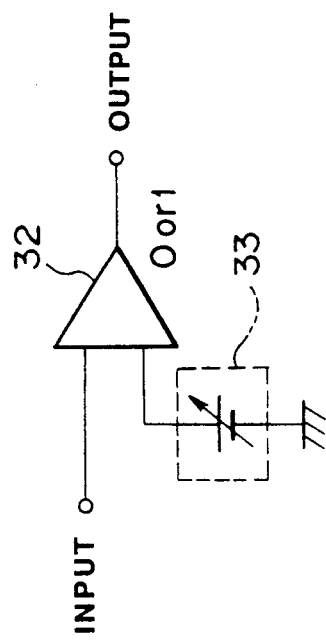

The above mentioned divaluing circuit 32 (representing 32a to 32c) and threshold level setting part 33 (representing 33a to 33c) are formed as shown, for example, in FIG. 3. The divaluing circuit 32 consists of a comparator and the threshold level setting part 33 consists of a variable voltage source. An image signal from the image input part 31 and a reference voltage by the above mentioned variable voltage source are applied to the above mentioned comparator at the input end. The output of the above mentioned comparator will be 0 when the image signal is above the threshold level but will be 1 when the image signal is below the threshold level.

The output signals of the above mentioned divaluing circuits 23a to 32c are input respectively into dark part extracting parts (1 to 3) 34a to 34c. this dark part extracting part 34 (representing 34a to 34c) makes the above mentioned divaluation on the respective pixels of the input image. When an image signal having brightness of respective valued pixels such as are shown, for example, in FIG. 4(a) has the threshold level of 3.5, an output 0 at a threshold level below 3.5 and an output of 0 at an threshold level above 3.5 to divalue the respective pixels, the image signal will be converted to a divalued image as shown in FIG. 4(b) in which the region of a pixel of 1 is a dark part. When the threshold level is thus set and the dark regions are thereby extracted, in case there are only odd darknesses such as shadows, the mistake of making the shadows an advancing direction will be able to be prevented.

Figures 5, 8:
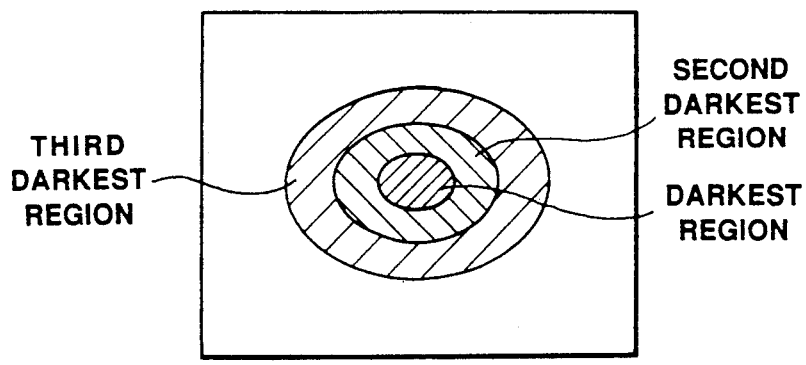

Examples of three dark regions thus extracted by the three dark part extracting parts 34a to 34c are shown in FIG. 5.

As a method of extracting dark parts, the method mentioned in U.S. Pat. No. 4,910,590 may be used.

When extracting dark parts, in order to remove the dark parts of extremely small regions by a break or the like of the fibers of the image guide, as data of some pixels, the average value of the data of pixels around that pixel may be used. Dark parts of small areas may be excluded.

The output signal of one dark part extracting part (1) 34a is input into a pattern comparing part 35 which correlates between the image from the above mentioned dark part extracting part (1) 34a and the comparative pattern stored in the pattern memorizing part 36 and determines the correlative value above the set value to be of a similar pattern. If the divalued data is represented by $a_{n,m}$, comparative pattern data are represented by $C_{n,m}$ and the set value is represented by K, the condition of being a similar pattern will be given by the following formula:

$$\sum_n \sum_m (c_{n,m} - a_{n,m})^2 < K$$

In case a pattern as is shown, for example, in FIG. 6 is made by the dark part extraction or in case the entire region becomes dark, the tip of the endoscope 1 will be shown to have come too close to an inspected object such as a mucous membrane and therefore, in the above mentioned pattern comparing part 35, a pattern will be recognized and a signal directing the endoscope to retreat will be output. In case the endoscope 1 at the tip contacts the mucous membrane, the entire visual field will become very dark but, in case the endoscope 1 at the tip is a little separated, the light from the two illuminating lenses will come in and therefore, as shown in FIG. 6, arcuate bright parts will be made at both ends of the visual field. Examples of comparative patterns for recognizing a pattern as is shown in FIG. 6 are shown in FIGS. 7(a) and 7(b). A plurality of such comparative patterns may be set.

The output signal of the above mentioned pattern comparing part 35 is selectively input into either of an endoscope retreat directing means 37 and boundary extracting part (1) 39 through a switching switch 38 of one input and two outputs. In case a pattern similar to the comparative pattern is recognized in response to the compared result of the above mentioned pattern comparing part 35, the above mentioned switching switch 38 will be switched to the endoscope retreat directing means 37 side and a signal directing to retreat the endoscope from the pattern comparing part 35 will be input into the above mentioned endoscope retreat directing means 37 which will control the endoscope 1 insertion driving part 7 to retreat the insertable part 2.

In case no pattern similar to the comparative pattern is recognized, the above mentioned switching switch 38 will be switched to the boundary extracting part (1) 389a side and the divalued image from the dark part extracting part (1) 34A will be input into the above mentioned boundary extracting part (1) 39a.

The output signals of the other dark part extracting parts (2 and 3) 34b and 34c are input respectively into the boundary extracting parts (2 and 3) 39b and 39c. In this boundary extracting part 39 (39a to 39c), for the respective lines of the above mentioned divalued image, a coordinate in which the divalued data vary from 0 to 1 or from 1 to 0 is determined, the boundary data of that coordinate is made 1 and the boundary of the other coordinate is made 0. When the divalued data for the n-th line and m-th line pixels are made $a_{n,m}$, the boundary data $b_{n,m}$, will be given by the following formula:

$$b_{n,m} = |a_{n,m-1} - a_{n,m}|$$

An example of an image having the boundary extracted for the divalued image shown in FIG. 4(b) is shown in FIG. 8. In order to make the process easy, 0 is input into the first row.

The output signals of the above mentioned boundary extracting parts 39a to 39c are input respectively into center extraction operating parts (1 to 3) 41a to 41c. The center coordinate of the extracted dark part is extracted in this center extraction operating part 41 (representing 41a to 41c). As shown, for example, in FIG. 9, in the data of the extracted dark part, the uppermost line and lowermost line of the lines in which the pixels of data of 1 are present are extracted and the average value (Y1+Y2)/2 of the Y coordinates Y1 and Y2 of these two lines is made a Y axis center coordinate. Likewise, the extreme left row and extreme right row of the rows in which the pixels of data of 1 are present are extracted and the average value (X1+X2)/2 of the X coordinates X1 and X2 of these two rows is made an X axis center coordinate.

As a method of extracting the center coordinate of the dark part, the number N of the pixels contained in the dark part is determined, the pixels contained in the dark part are counted sequentially in the X axis direction from above and the Y coordinate when the number becomes N/2 may be made a Y axis center coordinate and, in the same manner, the pixels contained in the dark part are counted sequentially in the Y axis direction from the left and the X coordinate when the number becomes N/2 may be made an X axis center coordinate.

The output signals of the above mentioned center extraction operating part 41a to 41c are input into a center position comparing part 42 in which, for the respective center coordinates $P_1 (x_1, y_1)$, $P_2 (x_2, y_2)$ and $P_3 (x_3, y_3)$ of the three regions (dark parts) extracted in response to three threshold levels, $$(X_1, Y_1) = (x_2 - x_1, y_2 - y_1)$$

and $(X_2, Y_2) = (x_3 - x_2, y_3 - y_2)$ are calculated.

The above mentioned $P_1$, $P_2$ and $P_3$ are in the darker order of the threshold levels.

Thus, in the center position comparing part 42, the variation of the center coordinates of the respective regions is detected.

The output signal of the above mentioned center position comparing part 42 is input into an endoscope progress directing means 43 which sets the endoscope progress direction in the $P_3$ $(x_3, y_3)$ direction and sets the endoscope progress speed according to the following conditions wherein $k_1$ and $k_2$ represent predetermined set values:

(1) If
$(X_1^2 + Y_1^2)^{\frac{1}{2}} < k_1$ and
$(X_2^2 + Y_2^2)^{\frac{1}{2}} < k_2$ a high speed.

(2) If
$(X_1^2 + Y_1^2)^{\frac{1}{2}} > k_1$ and
$(X_2^2 + Y_2^2)^{\frac{1}{2}} > k_2$ medium speed.

(3) If
$(X_2^2 + Y_2^2)^{\frac{1}{2}} > k_2$ a low speed.

The information of such endoscope inserting conditions (progress directions and progress speeds) is input into the insertion driving part 7 of the endoscope 1 through a switch 45. This insertion driving part 7 directs the curvable part 6 of the endoscope 1 in the above mentioned progress direction and advances the insertable part at the above mentioned progress sped.

A current source of a voltage V is connected to the above mentioned switch 45 at the control signal input and through a resistance 46. Also, this current source can be grounded through an operator operating switch 47 provided in the operating part 3 or the like of the endoscope 1. Therefore, the above mentioned switch 45 is on-off in response to the on-off of the operator operating switch 47 so that, when the operator wants to stop the insertion of the endoscope, when the above mentioned operator operating switch 47 is switched off, the switch 45 will be off and the insertion will be stopped.

The above mentioned insertion driving part 7 can be not only controlled by the automatic inserting apparatus but also manually operated.

This embodiment has been explained, for convenience sake, with the number of pixels of 5×5 but is the same with more pixels.

The operation of this embodiment shall be explained in the following with reference to FIGS. 10 and 11.

An endoscope image imaged by the solid state imaging device 12 of the endoscope 1 is input into the automatic inserting apparatus 30 through the image input part 31 and is divalued on three different threshold levels by the divaluing circuit 32 and dark part regions corresponding to the respective threshold levels are extracted in the dark part extracting part 34. The boundaries of the regions are extracted by the boundary extracting part 39 and centers of the respective regions are determined by the center extraction operating part 41. The center positions of the respective regions are compared in the center position comparing part 42 and, in response to the results, the endoscope inserting conditions are set by the endoscope progress directing means 43 and, according to these inserting conditions, the endoscope 1 is inserted by the insertion driving part 7.

In case a specific pattern is recognized in the pattern comparing part 35, the endoscope 1 will be retracted.

Figure 10A:
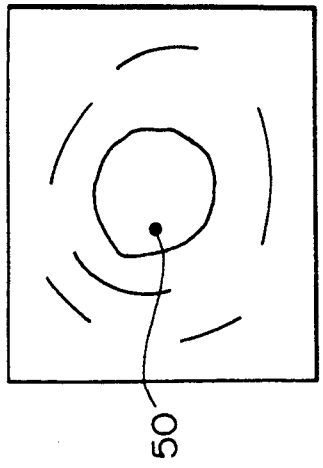
FIGS. 10(a) to 10(c) are explanatory views for explaining the operation of this embodiment in case the tube cavity is linear.
Figure 10B:
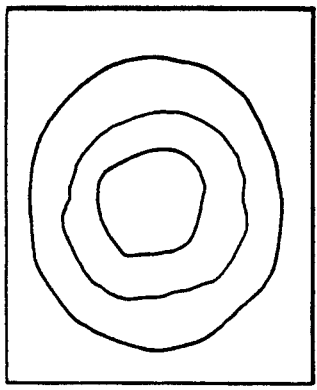
Figure 10C:
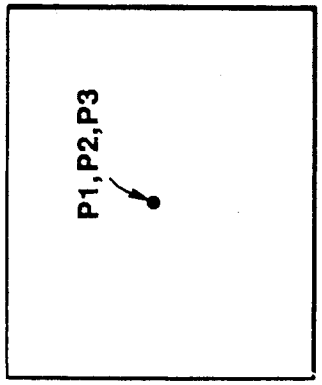

In case the tube cavity 50 into which the endoscope 1 is to be inserted is linear, the endoscope image will be as shown in FIG. 10(a) and the boundaries of the respective regions will be as shown in FIG. 10(b). In FIG. 10(b), the farther inside the region, the darker the region is. In such a case, as shown in FIG. 10(c), the centers $P_1$, $P_2$ and $P_3$ of the respective regions will substantially coincide with one another. In such a case, as the endoscope may progress at a high speed, the above mentioned endoscope progress directing means 43 will set the progress direction in the $P_3$, direction and the progress speed at a high speed.

Figure 11A:
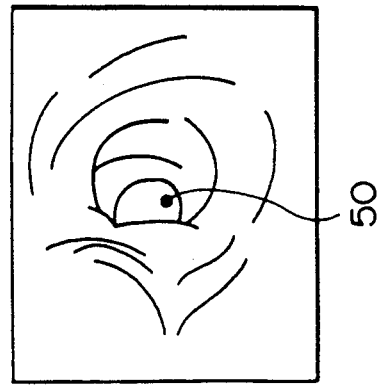
FIGS. 11(a) to 11(c) are explanatory views for explaining the operation of this embodiment in case the tube cavity is curved.
Figure 11B:
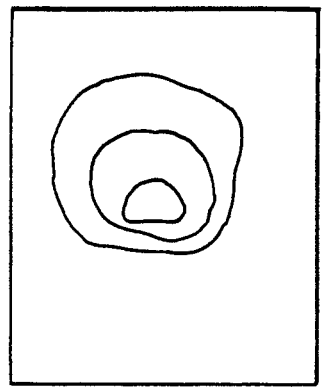
Figure 11C:
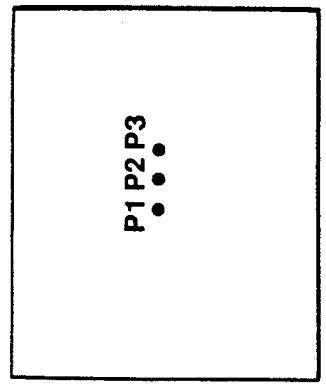

On the other hand, in case the tube cavity 50 into which the endoscope 1 is to be inserted is curved, the endoscope image will be as shown in FIG. 11(a) and the boundaries of the respective regions will be as shown in FIG. 11(b). In FIG. 11(b), the farther inside the region, the darker the region is. In such a case, as shown in FIG. 11(c), the centers $P_1$, $P_2$ and $P_3$ of the respective regions will lag in response to the curvature. In such a case, the endoscope must be advanced in response to the curvature of the tube cavity. Therefore, the above mentioned endoscope progress directing means 43 sets the progress direction in the $P_3$, direction and sets the progress speed at a medium speed or low speed according to the above mentioned condition (2) or (3).

In the case the centers of the respective regions lag as in FIG. 11(c), the progress direction may lag in the order of $P_3$, $P_2$ and $P_1$ in progress.

Thus, according to this embodiment, the state of the object to be inspected is discriminated and a proper inserting condition corresponding to the state is set so that the endoscope may be automatically and easily inserted.

In this embodiment, the discriminated endoscope inserting condition is used to automatically insert the endoscope but may be utilized so that the operator may insert the endoscope.

In case the operator is to insert the endoscope, for example, into large intestines, if the endoscope is pushed in when the tip part of the insertable part 2 of the endoscope is before the bent part of the large intestines 60 as shown in FIG. 12(a), the tip part of the insertable part 2 will butt against the large intestine wall as shown in FIG. 12(b). In such a case, as the insertable part 2 is fine, a local force will be applied to a part of the large intestine wall, a pain will be given to the patient and the large intestine wall will be pushed to obstruct the insertion of the endoscope.

Therefore, two methods of making it easy to insert the endoscope into a large intestines or the like shall be shown in the following.

Figure 13A:
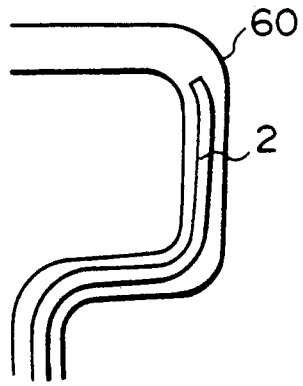
FIGS. 13(a) to 13(e) and FIGS. 14(a) to 14(3) are explanatory views of methods of making it easy to insert the endoscope.
Figure 13B:
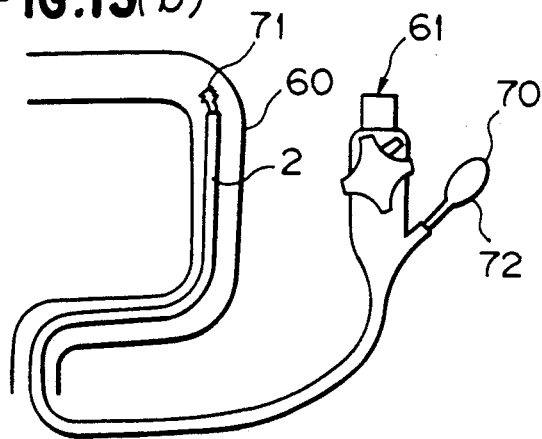
Figure 13:
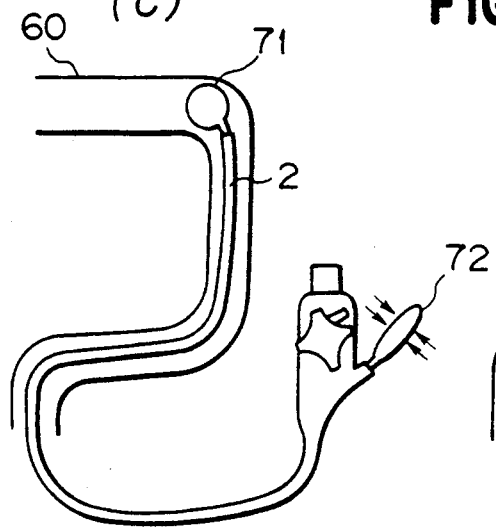

The first method is shown in FIGS. 13. In this method, as shown in FIG. 13(a), the insertable part 2 of an endoscope 61 having a treating instrument channel is inserted into large intestines 60 and, as shown in FIG. 13(b), a balloon treating instrument 70 is inserted into the above mentioned treating instrument channel. This balloon treating instrument 70 has a tip balloon 71 on the tip side and a hand base operating side balloon 72 on the hand base side and both balloons 71 and 72 communicate with each other. With the tip balloon 71 contracted, this balloon treating instrument 70 is inserted into the above mentioned treating instrument channel through a treating instrument inserting port and the, contracted tip balloon 71 is projected out of the tip part of the insertable part 2. The tip balloon 71 is made slippery on the surface. A jelly or the like may be applied for that purpose.

Figure 13D:
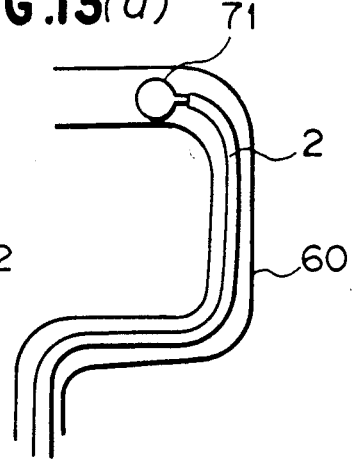

Then, as shown in FIG. 13(c), the tip balloon 71 is inflated by gripping and contracted the hand base operating side balloon 72. In this state, as shown in FIG. 13(d), the endoscope is pushed in. Then, as the tip balloon 71 is large in the contact surface with the large intestines and is slippery, the endoscope can be smoothly inserted without giving a pain to the patient.

Figure 13E:
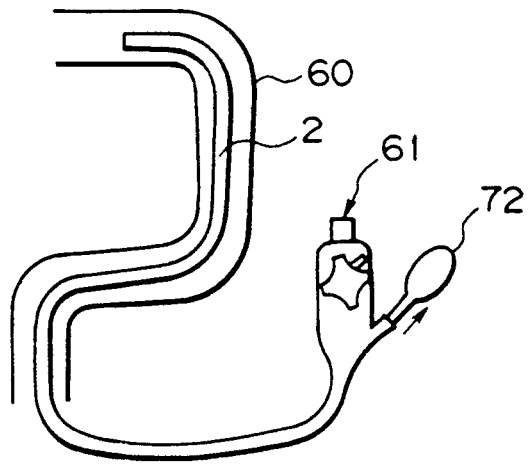

In the observation, as shown in FIG. 13(e), the tip balloon 71 is contracted by inflating the hand base operating side balloon 72 gripped and contracted by hand and is pulled out until it disappears from the visual field of the endoscope.

By repeating the states in FIGS. 13(b) to 13(e), the endoscope is inserted.

The second method is shown in FIGS. 14. In this method, the same as in the first method, as shown in FIG. 14(a), the insertable part 2 of the endoscope 61 having the treating instrument channel is inserted into the large intestine 60 and, as shown in FIG. 14(b), the balloon treating instrument 70 is inserted into the above mentioned instrument channel. In the balloon treating instrument 70 in this case, the diameter of the tip balloon 71 when inflated is larger than the inside diameter of the large intestines 60. With the tip balloon 71 contracted, this balloon treating instrument 70 is inserted into the above mentioned treating instrument channel through the treating instrument inserting port. Then the contracted tip balloon 71 is projected out of the tip part of the insertable part 2. In this case, the projection is made larger than in the case of the above mentioned first method.

Figure 14A:
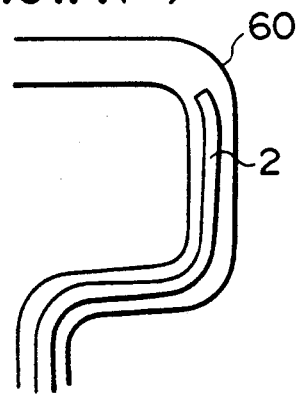
Figure 14B:
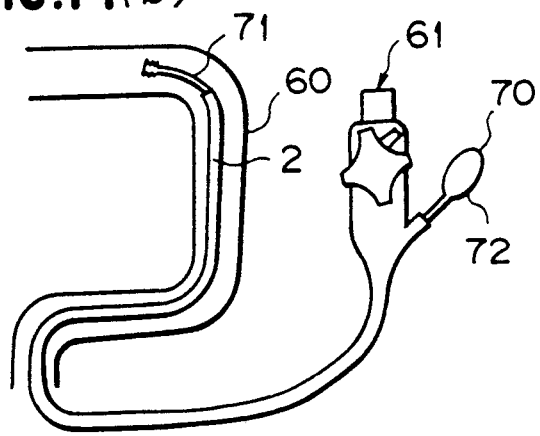
Figure 14C:
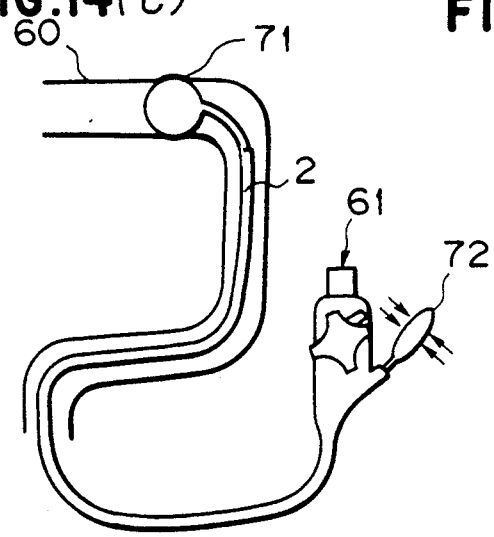
Figure 14D:
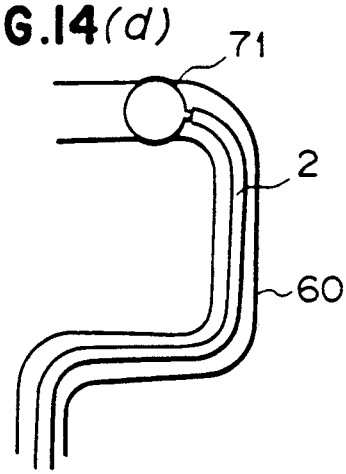

As shown in FIG. 14(c), the tip balloon 71 is inflated by gripping and contracting the hand base operating side balloon 72. As the diameter of the tip balloon 71 is larger than the inside diameter of the large intestines 60, the tip balloon 71 will be fixed. In this state, as shown in FIG. 14(d), the endoscope is inserted with the balloon treating instrument 70 as a guide. Thereby, the endoscope can be inserted without contacting the tip part of the insertable part 2 with the large intestine wall.

Figure 14E:
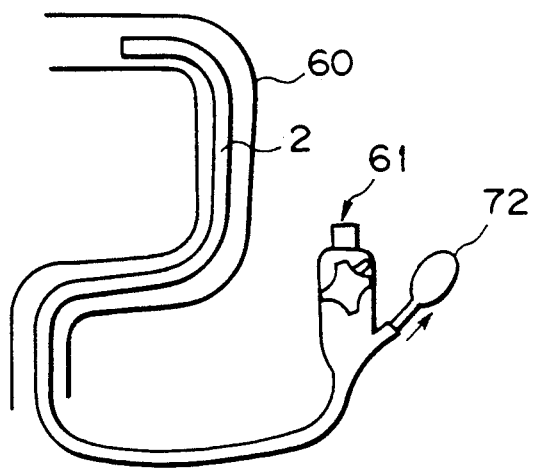

In the observation, as shown in FIG. 14(e), by inflating the hand base operating side balloon 72 gripped and contracted by hand, the tip balloon 71 is contracted and is pulled out until it disappears from the visual field of the endoscope.

By repeating the states in FIGS. 14(b) to 14(e), the endoscope is inserted.

As in the above two examples, by inserting the endoscope with the balloon as a guide, the insertion is made easy.

FIG. 15 shows an example of an endoscope wherein it can be known that the tip part of the insertable part of the endoscope as butted against an object to be inspected such as the large intestines.

In this endoscope, a hood 85 is fitted to the tip part 80 of the insertable part 2 by a plurality of springs 86 so as to be rockable by an external force. An observing window 81 of the endoscope is positioned in the center of the tip part and illuminating windows 82 are arranged around this observing window 81. The visual field angle of an objective optical system provided inside the above mentioned observing window 81 and the visual field angle of an objective optical system regulated by the tip opening part of the above mentioned hood 85 substantially coincide with each other.

In such a formation, when the hood 85 is subjected to an external force, the hood 85 will be pushed on the side subjected to the external force and will incline. A part of the visual field of the objective optical system will be eclipsed. The side subjected to the external force can be determined and thereby the direction in which to proceed can be known.

In FIGS. 16 to 19 is shown the second embodiment of the present invention.

This embodiment is an example in which a histogram relating to the brightness levels of an endoscope image is utilized to set the threshold levels of divaluing circuits 32a to 32c.

Figure 19A:
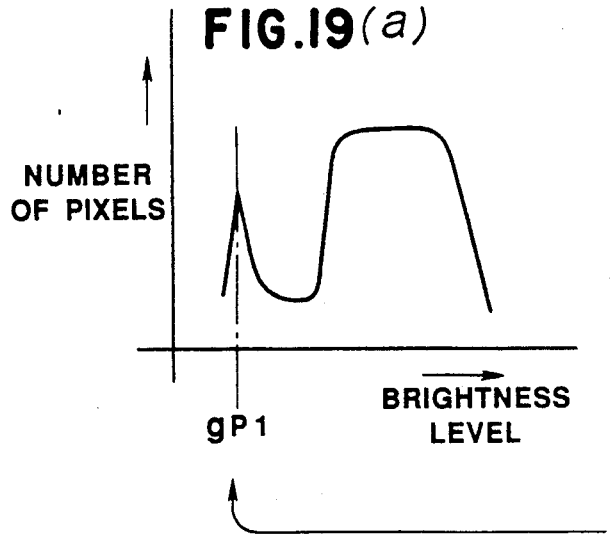
FIG. 19(a) is a histogram of brightness levels of an endoscope image.
Figure 19B:
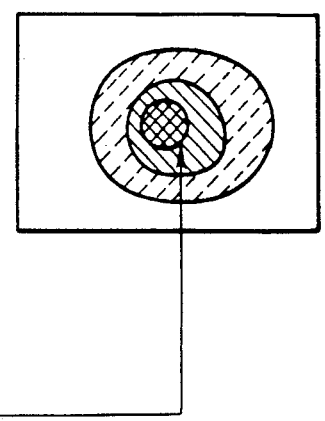
FIG. 19(b) is an explanatory view showing an endoscope image.

As a result of investigating some endoscope photographs, it has been found that, in an endoscope image as is shown in FIG. 19(b), a histogram relating to brightness levels as is shown in FIG. 19(a) is obtained and the first peak (as seen from the darker side) in this histogram corresponds to the dark region of the endoscope image for determining the endoscope inserting direction. FIG. 19(a) is a histogram showing numbers of pixels of respective brightness levels and FIG. 19(b) shows an endoscope image which gets darker as the center is approached.

Therefore, the above mentioned threshold level may be set from the value of the brightness level of the first peak of the histogram. For example, as shown in FIG. 19(a), if the brightness level (gray level) of the first peak is $g_{p1}$, the threshold level for setting the darkest region among a plurality of regions corresponding to the brightness will be set at $g_{p1}$.

The formation of an endoscope automatically inserting apparatus utilizing a histogram to set threshold levels is shown in FIG. 16.

In this apparatus, an image signal from an image input part 31 is input into divaluing circuit 32a to 32c, is converted to a digital signal by an A/D converter 101 and is then input into a histogram preparing part 102 in which the total number of pixels of respective brightness levels of an endoscope image is determined to prepare a histogram as is shown in FIG. 19(a). The brightness level $g_{p1}$ of the first peak of the histogram prepared in this histogram preparing part 102 is detected in a first peak detecting part 103. The brightness level $g_{p1}$ of the first peak detected in this first peak detecting part 103 is input into respective threshold level setting parts (1 to 3) 33a to 33c.

Figure 17:
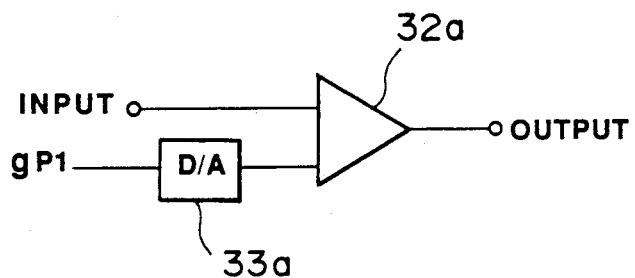

The threshold level setting part (1) 33a for setting the darkest region consists of a D/A converter as shown, for example, in FIG. 17 and converts the above mentioned brightness level $g_{p1}$ to an analogue voltage which is applied to one input end of a comparator forming the divaluing circuit 32a.

Figure 18:
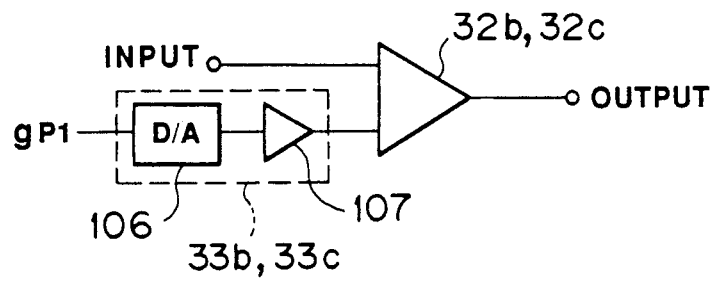

Each of the threshold level setting parts (2) 33b and (3) 33c for setting the other regions consists of a D/A converter 106 converting the above mentioned brightness level $g_{p1}$ to an analogue voltage and an amplifier 1207 multiplying the output of this D/A 106 by a predetermined factor larger than 1 as shown, for example, in FIG. 18 and applies the output of the above mentioned amplifier 107 to one input end of a comparator forming each of the divaluing circuits 32b and 32c.

The threshold level of the darkest region is set at $g_{p1}$ and the threshold levels of the other regions are set at values larger than $g_{p1}$.

When setting the threshold levels of the other regions, a predetermined value may be added to $g_{p1}$.

Thus, according to this embodiment, proper threshold levels adapted to the endoscope image can be set and the disadvantage that, as the threshold levels are not properly set, the inserting direction can not be correctly detected can be avoided.

The other formations, operations and effects are the same as in the first embodiment.

Figure 20:
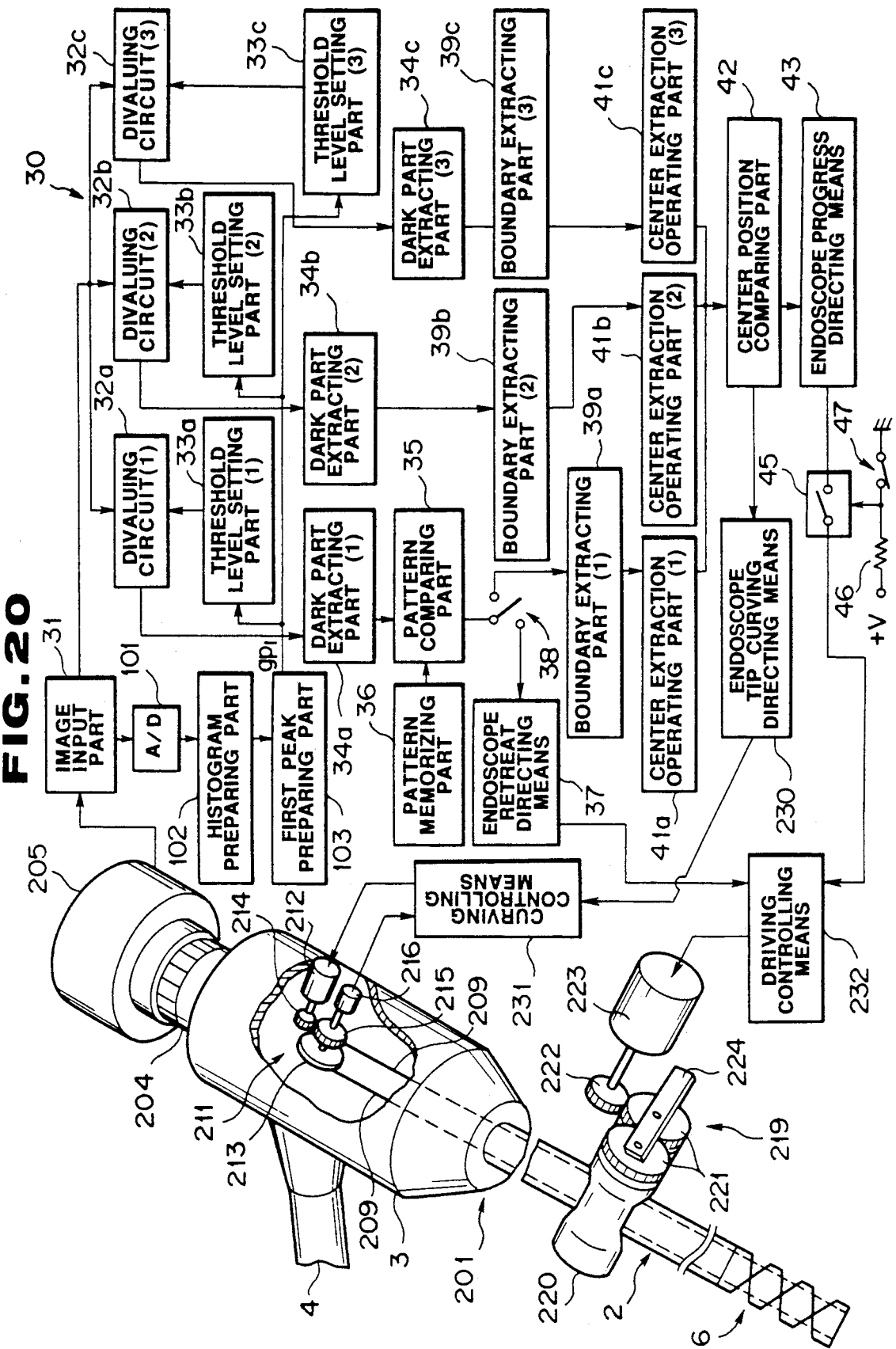
FIG. 20 is a block diagram showing the formation of an endoscope automatically inserting apparatus of the third embodiment of the present invention.

FIG. 20 shows the third embodiment of the present invention.

An endoscope 201 to be used in this embodiment is a fiber scope comprising an insertable part 2, an operating part 3 and a universal cord 4 extended from the operating part 3 and connected to a light source apparatus (not illustrated). An eyepiece part 204 is provided in the rear end part of the operating part 3 and is fitted with a television camera 205.

The tip surface of an image guide (not illustrated) is arranged instead of a solid state imaging device in the image forming position of an objective lens of the above mentioned endoscope 201. This image guide is inserted through the insertable part 2 and operating part 3 and is opposed on the rear end surface to an eyepiece lens (not illustrated) within the above mentioned eyepiece part 204. An object image formed by the objective lens is transmitted to the eyepiece part 204 by the image guide 204 and is imaged by the television camera 205 fitted to this eyepiece part 204. The output signal of the above mentioned television camera 205 is input into the image input part 31 of the automatic inserting apparatus 30 through a video signal processing circuit (not illustrated).

A plurality of angle wires 209 are inserted through the insertable part 2, are fixed at the tips to the curvable part 6 at the tip and are wound at the rear ends onto a pulley 213 within a curving driving part 211 provided within the operating part 3. A gear 215 is fitted to the rotary shaft of this pulley 213 and is meshed with a gear 214 fitted to the output shaft of a motor 212 provided within the operating part 3. A potentiometer 216 is fitted to the rotary shaft of the above mentioned pulley 213. This potentiometer 216 and the above mentioned motor 212 are connected to a curving controlling means 231 within the automatic inserting apparatus 30. This curving controlling means 231 is connected to an endoscope tip curving directing means 230 within the automatic inserting apparatus 30. This endoscope tip curving directing means 230 is connected to a center position comparing part 42.

An insertable part advancing and retreating apparatus 219 is fitted to the insertable part 2, is rotatably fitted to a fitting plate 224 and has two rollers 220 holding the insertable part 2 on both sides. Gears 221 meshing with each other are fitted respectively to these two rollers 220 at the ends so as to rotate in the directions reverse to each other to advance and retreat the insertable part 2 held between the two rollers 220 as a result. AS gear 222 fitted to the output shaft of a motor 223 is meshed with one gear 221. The above mentioned motor 223 is connected to a driving controlling means 232 within the automatic inserting apparatus 30. This driving controlling means 232 and an endoscope retreat direction means 37 are connected to an endoscope progress directing means 43 through a switch 45.

The other formations are the same as in the second embodiment.

The operation of this embodiment shall be explained in the following.

An endoscope image imaged by the television camera 205 is input into the automatic inserting apparatus 30, a plurality of dark regions corresponding to a plurality of threshold levels are extracted by the same operation as in the first embodiment or second embodiment and endoscope inserting conditions are set by the endoscope progress directing means 43 in response to the arrangement of the center positions of the respective regions. The progress directing signal of this endoscope progress directing means 43 is transmitted to the driving controlling means 232 through the switch 45 to drive the motor 223. By the drive of this motor 223, the rollers 220 are rotated and the insertable part 2 is advanced.

In the same manner, the directing signal of the endoscope retreat directing means 37 is transmitted to the above mentioned driving controlling means 232 to reversely rotate the motor 223 and retreat the insertable part 2.

The output of the center position comparing part 42 is input into the endoscope curving directing means 230. In case the center position of the dark part region lags from the center of the endoscope image, the above mentioned endoscope tip curving directing means 230 will output a curving directing signal to the curving controlling means 231. The center position of the dark part region to be used to control curving may be one of the respective center coordinates $P_1$, $P_2$ and $Phd 3$, of three dark part regions corresponding to three threshold level or may be determined on the basis of two or more of them. The above mentioned curving controlling means 231 rotates the motor 212 in response to the above mentioned curving directing signal. Thereby, the wires 209 are pushed and pulled through the pulley 213 to curve the curvable part 6. The rotation of the above mentioned pulley 213 is detected by the potentiometer 213 and is fed back to the curving controlling means 231 so that the curvable part 5 may be cured to a curving angle predetermined by the curving directing signal. Only the curving driving part 211 for two directions is shown in the drawing but a curving control in four directions is possible by providing two sets of the curving driving parts 211.

The other operations and effects are the same as in the first embodiment or second embodiment.

In the third embodiment, for the endoscope, an electronic endoscope having a solid state imaging device in the tip part of the insertable part may be used the same as in the first embodiment.

FIGS. 21 to 25 show the fourth embodiment of the present invention.

In this embodiment, a self-running type insertable body provided in the tip part of the insertable part is used instead of the insertable part advancing and retreating apparatus 219 of the third embodiment.

Figure 21:
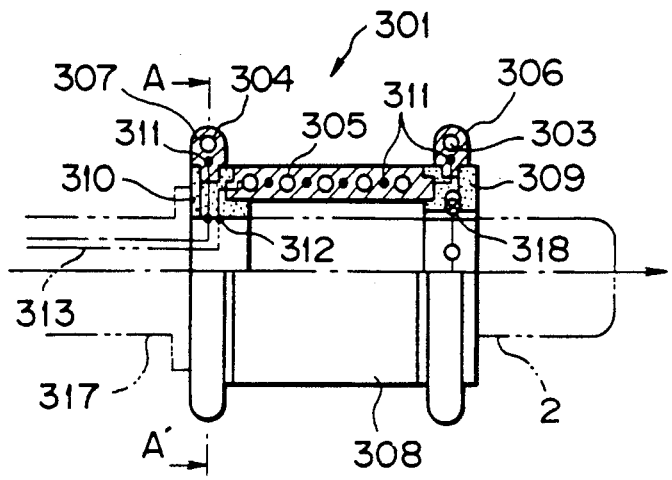
Figure 22:
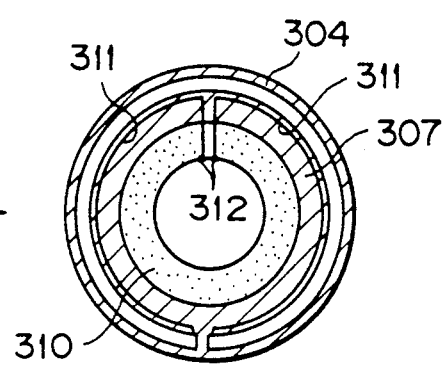

As shown in FIG. 21, a self-running type insertable body 301 is to be fitted to the tip part of the insertable part 2 of the endoscope and comprises a pair of front and rear loop-like members 303 and 304 and a transformable member 305 arranged between these loop-like members 303 and 304 and these respective members 303, 304 and 305 are formed respectively of both directional shape memorizing alloys. The above mentioned transformable member 305 is formed to be coil-like. The above mentioned loop-like members 304 and 303 have memorized shapes in either of the autenite phase and martensite phase, will transform to enlarge the diameter of their externally contacting circle when heated to be above the transforming temperature transforming the martensite phase to the austenite phase and will transform to reduce the diameter of their externally contacting circle when cooled to be below the transforming temperature transforming the austenite phase to the martensite phase. The transformable member 305 will transform to extend in its entirety when heated to be above the transforming temperature transforming the martensite phase to the austenite phase and will transform to contract in its entirely when cooled to be below the transforming temperature transforming the austenite phase to the martensite phase.

The above mentioned loop-like members 303 and 304 are embedded respectively in ring-like elastic cover bodies 306 and 307 and the transformable member 305 is embedded in a tubular cover body 308. The above mentioned respectively corresponding cover bodies 306 and 307 are connected respectively through connecting ring bodies 309 and 310 to this cover body 308 respectively at the front and rear ends.

Figure 23:
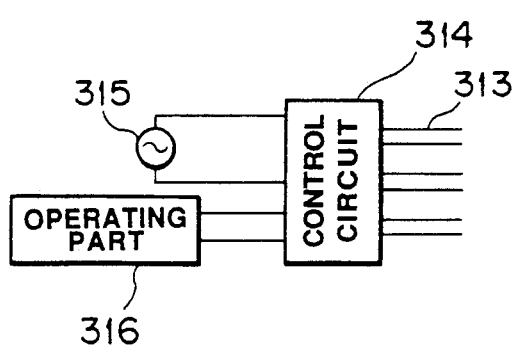

Lead wires 311 are connected respectively to the above mentioned loop-like members 303 and 304 and transformable member 305. The lead wires 31 connected to these respective members 303, 304 and 305 are connected to respective contacts 312 provided on the inner surface of the rear connecting ring body 310 respectively through the cover bodies 306, 307 and 308. These respective contacts 312 contact the contacts provided on the outer peripheral surface of the endoscope insertable part 2 so as to be electrically connected. These respective contacts 312 are connected to a control circuit 314 of an electrifying means as is shown in FIG. 23 through lead wires 313 arranged within the insertable part 2. A current source 315 and operating part 316 are connected to this control circuit 314 so that the electrifying order, electrifying time and output for the respective members 303, 304 and 305 may be set by the operating part 316. The above mentioned control circuit 314 is connected also to the endoscope progress directing means 43 through the endoscope retreat directing means 37 and switch 45 in FIG. 20 so that the electrifying order, electrifying time and output for the respective members 303, 304 and 305 may be set in response to the directing signals from the endoscope retreat directing means 37 and endoscope progress directing means 43.

As shown in FIG. 21, the rear connecting ring body 310 is fixed to the fixing part 317 of the endoscope insertable part 2. The front connecting ring body 309 is provided on the inner surface with a ball bearing part 3189 so as to be slidable on the peripheral surface of the insertable part 2.

The other formations are the same as in the third embodiment.

The operation of this embodiment shall be explained in the following.

First of all, as shown in FIG. 21, the endoscope insertable part 2 is fitted with a self-running type insertable body 301 and is inserted into a body cavity or piping which is a part into which the insertable part is to be inserted. At this time, as no electric current is passed, the respective loop-like members 303 and 304 and transformable member 305 have respectively contracted so as to be comparatively easily insertable.

Figure 24:
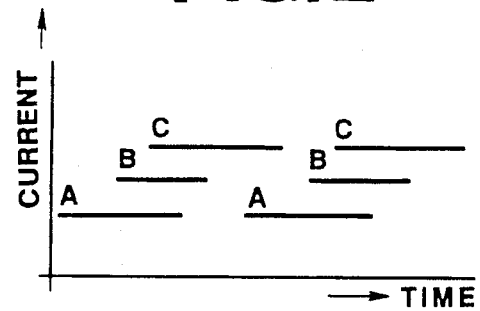
Figures 25A, 25B, 25C:
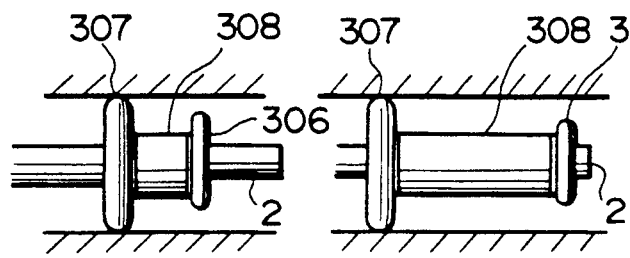
FIG. 25(a) to 25(e) are explanatory views showing the operation of the self-running type inserting body.
Figure 25D:
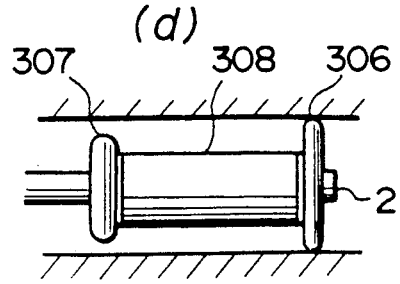
Figure 25E:
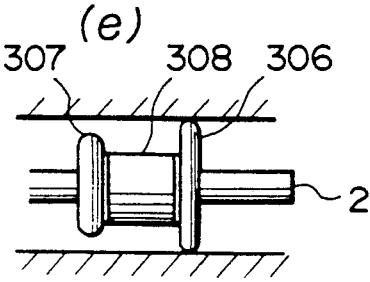

An endoscope image is input into the automatic inserting apparatus 30. By the same operation as in the first embodiment or second embodiment, the endoscope inserting conditions are set by the endoscope progress direction means 43. The progress directing signal of this endoscope progress directing means is transmitted to the control circuit 314 through the switch 45. This control circuit 314 advances the insertable part 2 as follows. First, the rear loop-like member 304 is electrified as shown by a waveform A in FIG. 24 to enlarge its outside diameter as shown in FIG. 25(a). Thereby, the cover body 307 covering the loop-like member 204 is held as pushed against the inner wall of the part into which the insertable part is inserted. While the above mentioned loop-like member 304 is electrified, as shown by a waveform B in FIG. 24, the transformable member 305 is also electrified so that, as shown in FIG. 25(b), the transformable member 305 may extend and the tip side loop-like member 303 may slide and advance on the outer periphery of the endoscope insertable part 2. As shown by a waveform C in FIG. 24, the tip side loop-like member 303 is electrified so that, as shown in FIG. 25(c), the outside diameter of the loop-like member 303 may become so large that the cover body 306 covering this loop-like member 303 may be held as pushed against the inner wall of the part into which the insertable part is inserted. Just after this, as shown in FIG. 24, the electrification (in waveform A) of the rear loop-like member 304 is stopped and then the electrification (in the waveform B) is also stopped so that the loop-like member 304 and transformable member 305 may be cooled and, as shown in FIGS. 25(d) to 25(e), the look-like member 304 and transformable member 305 may contact. Therefore, the cover body 307 covering the rear look-like member 304 will separate from the inner wall of the part into which the insertable part is inserted as shown in FIG. 25(d) and the transformable member 305 will contract to advance the rear loop-member 304 while pulling the endoscope insertable part 2. The electrification (in waveform C) of the front loop-like member 303 is stopped to contract the loop-like member 303. Thus, a one-stroke advancing operation is completed. By repeating this operation, the insertable part 2 is advanced.

The directing signal of the endoscope retreat directing means 37 is transmitted to the above mentioned control circuit 314 to retreat the insertable part 2. In the case of retreating the insertable part 2, the order of electrifying the loop-like members 304 and 304 and transformable member 304 may be made reverse to the case of advancing it.

The shape memorizing alloy to be used for the look-like members 303 and 304 and transformable member 305 may be unidirectional memorizing only an expanded diameter or extended shape and the loop-like members 303 and 304 and transformable member 305 may be contracted by the elastic returning force of the cover bodies 306, 307 and 308.

The other operations and effects are the same as in the third embodiment.

As explained above, according to the first to fourth embodiments, there are effects that, on the basis of the arrangement of a plurality of regions corresponding to brightness, endoscope inserting conditions corresponding to the state of the object to be inspected can be determined and a proper insertion corresponding to the state of the body into which the endoscope is inserted is possible.

Figure 26:
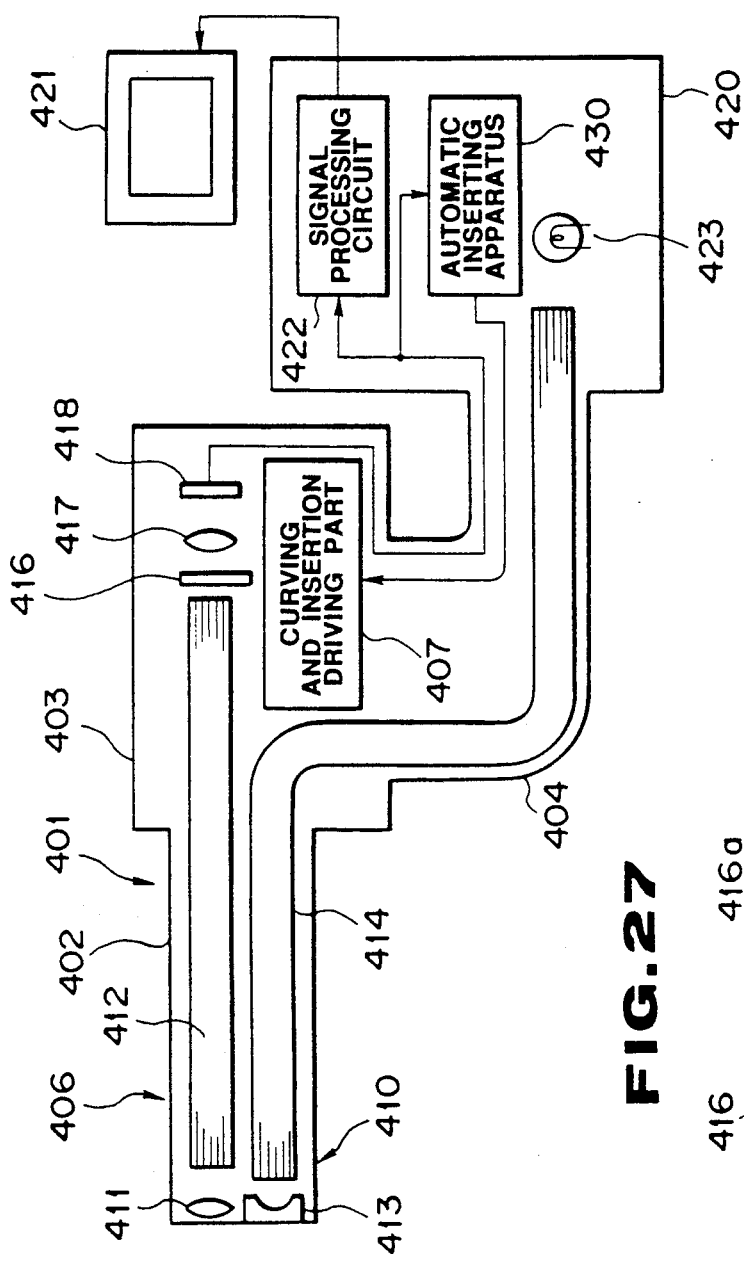
FIGS. 26 to 30 relate to the fifth embodiment of the present invention.
Figure 30:
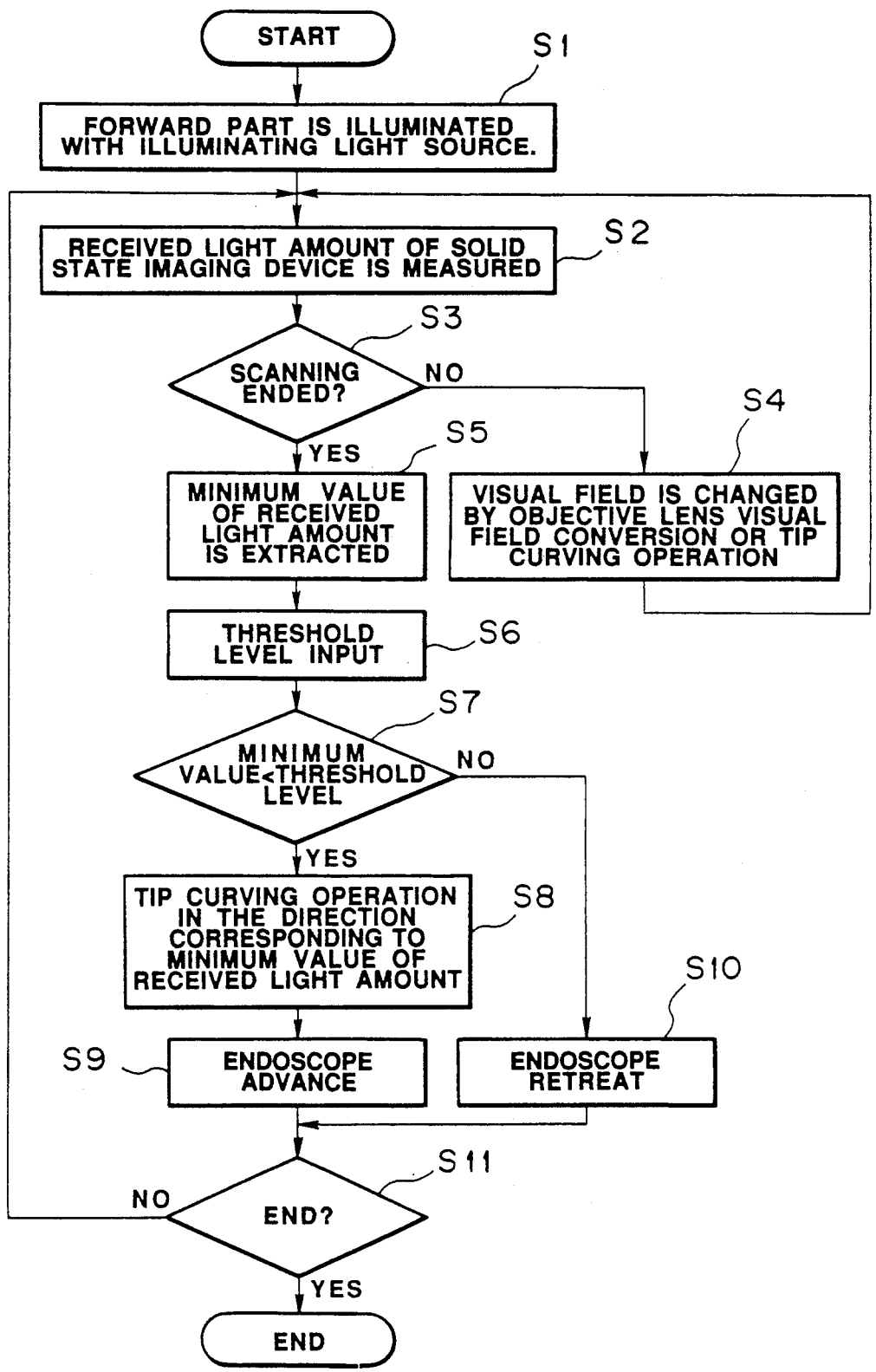

FIGS. 26 and 30 show the fifth embodiment of the present invention.

As shown in FIG. 256, an endoscope apparatus comprises an endoscope 401, a control apparatus 420 connected with this endoscope 401 and a monitor 421 connected to this control apparatus 420.

The above mentioned endoscope 401 comprises an elongate flexible insertable part 402 and an operating part 403 connected to this insertable part 402 at the rear end. A flexible universal cord 404 is extended sidewise from the above mentioned operating part 403 and is connected at an end to the above mentioned control apparatus 420.

A flexible curvable part 406 is provided on the tip side of the above mentioned insertable part 402 and is controlled to be curved by a curving and inserting driving means 407 provided in the endoscope 401. In order to curve the above mentioned curvable part 406, for example, a plurality of angle wires are inserted through the insertable part 402, are fixed at the tips to the tip side of the curvable part 406 and are pulled at the rear ends by a motor provided in the above mentioned curving and insertion driving means 407 so that the above mentioned curvable part 406 may be curved in any direction. For the curving means, an actuator using a shape memorizing alloy or the like may be provided within the above mentioned curvable part 406.

In this embodiment, by the above mentioned curving and insertion driving means 407, the insertable part 402 can be advanced. For this insertable part 402 advancing means, there can be used, for example, a means shown in the publication of Japanese patent application Laid Open No. 41635/1987 and the means shown in the third or fourth embodiment of the present invention.

An observing window and illumination window are provided in the tip part 410 of the above mentioned insertable part 402. Inside the above mentioned observing window, an objective lens 411 is provided and the tip surface of an image guide 412 made of a fiber bundle is arranged in the imaging forming position of this objective lens 411. This image guide 412 is inserted through the above mentioned insertable part 402 and is extended to the above mentioned operating part 403. Within the above mentioned operating part 403, as opposed to the rear end surface of the above mentioned image guide 412, a visual field mask 416, image forming lens 417 and solid state imaging device 418 are arranged in the order mentioned.

Figure 27:
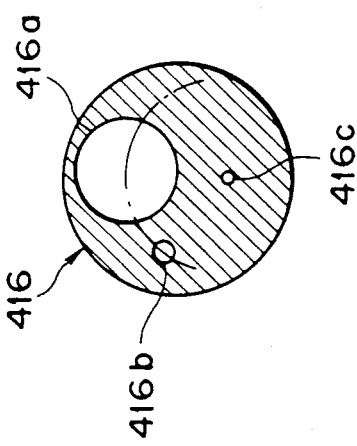

As shown in FIG. 27, the above mentioned visual field mask 416 has an ordinary observing window 416a of a large visual field for an ordinary observation and an automatically inserted lighting window 416b of a small visual field for an automatic insertion, is rotatable around a rotary shaft 416c as a center and can selectively oppose either of the above mentioned ordinary observing window 416a and automatically inserted light collecting window 416b to the rear end surface of the above mentioned image guide 412.

The signal lines connected to the above mentioned solid state imaging device 418 are inserted through the universal cord 404 and are connected to a signal processing circuit 422 and automatic inserting apparatus 430 provided in the above mentioned control apparatus 420. Inside the above mentioned illuminating window, a light distributing lens 413 is provided and a light guide 414 consisting of a fiber bundle is connected to this light distributing lens 413 at the rear end, is inserted through the above mentioned insertable part 402, operating part 403 and universal cord 404 and is connected at the entrance end to the above mentioned control apparatus 420 so that an illuminating light emitted from a light source apparatus 423 provided in this control apparatus 420 may enter the above mentioned light guide 414 at the entrance end.

The above mentioned solid state imaging device 418 is driven by the above mentioned signal processing circuit 422 and the output signal of this solid state imaging device 418 is processed to be a video signal by the above mentioned signal processing circuit 422. The video signal output from this signal processing circuit 422 is input into a monitor 421 in which an object image is displayed.

Figure 28:
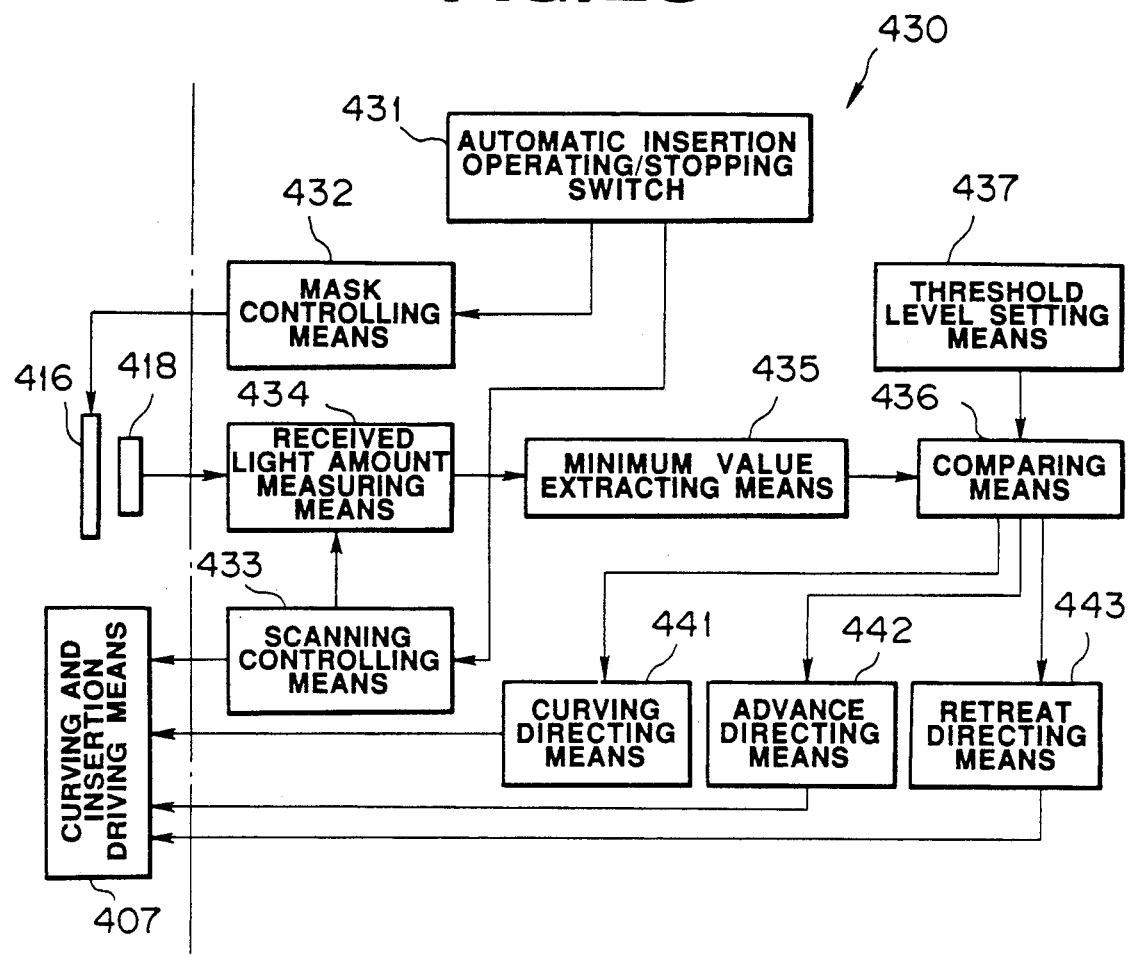

The above mentioned automatic inserting apparatus 430 shall be explained in the following with reference to FIG. 28.

The above mentioned automatic inserting apparatus 430 comprises a mask controlling means 432 rotating a visual field mask 416 of the endoscope 401, a scanning controlling means 433 controlling the curving and insertion driving means 407 and scanning the visual field by the automatically inserted light collecting window 416b. An automatic insertion operating/stopping switch 431 operates the above mentioned mask controlling means 432 and scanning controlling means 433. The above mentioned mask controlling means 432 is operatively connected with the automatic insertion operating/stopping switch 431 to rotate the visual field mask 416 so that, at the time of the automatic inserting position, the automatically inserted lighting window 416b may be opposed to the image guide 412 on the rear end surface. The above mentioned visual field mask 416 may be manually rotated. At the time of automatic insertion, the above mentioned scanning controlling means 433 will control the curving and insertion driving means 407 to curve the curvable part 406 and will scan the visual field by the above mentioned automatically inserted lighting window 416b. For the visual field scanning means, a means of converting the visual field of the objective lens 411 may be provided.

Figure 29:
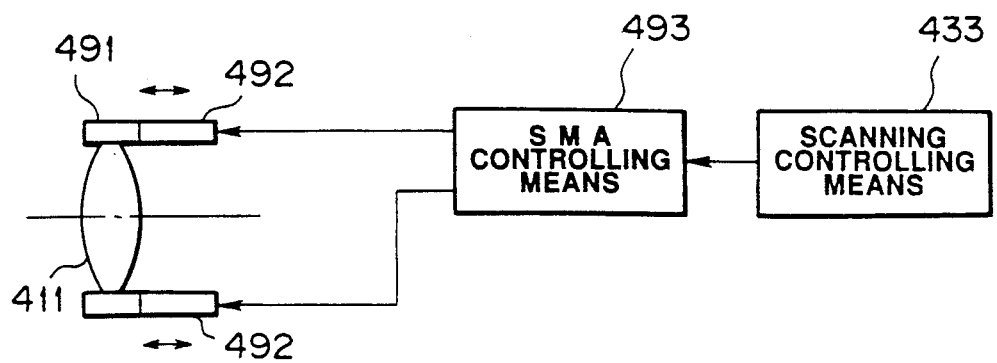

An example of the visual field converting means of the objective lens 411 is shown in FIG. 29. The objective lens 411 is supported by a supporting frame 491. Bar-like shape memorizing alloys (mentioned as SMA's hereinafter) 492 extending and contracting in the optical axis direction are fixed respectively at one end, for example, to four upper, lower, right and left places of this supporting frame 491, are fixed respectively at the other end to the tip part 410 of the insertable part 402 and are connected to an SMA controlling circuit 493 electrifying the respective SMA's 492 to be extended and contracted. By controlling the electrification of the respective SMA's 491 by this SMA controlling circuit 493, the optical axis of the objective lens 411 can be inclined in any direction and angle. The above mentioned SMA controlling circuit 493 is controlled by the scanning controlling means 433. At the time of automatic insertion, the above mentioned scanning controlling means 433 will control the SMA controlling circuit 493 to incline the optical axis of the objective lens 411 and will scan the visual field by the above mentioned automatically inserted lighting window 416b. By the means shown in FIG. 29, the objective lens 411 and image guide 412 may be directed together at the tips in any direction to scan the visual field.

A received light amount measuring means 434 measuring and storing the received light amount of the solid state imaging device 418 of the endoscope 401 is provided in the automatic inserting apparatus 430 and is controlled by the above mentioned scanning controlling means 433 so that, at the time of the automatic insertion, the received light amount of the solid state imaging device 418 in the respective visual field direction, when the visual field by the automatically inserted lighting window 416b is scanned by the above mentioned scanning controlling means 433, may be measured and may be stored in response to the respective visual field direction. The received light amount data in the respective visual field direction measured by the above mentioned received light amount measuring means 434 is input into a minimum value extracting means 435 by which the minimum value of the received light amount of the above mentioned solid state imaging device 418 is extracted. The minimum value data, extracted by the above mentioned minimum value extracting means 435, is compared by a comparing means 436 with the threshold level set in advance by the threshold level setting means 437. The results of the comparison by this comparing means 436 are input into a curving directing means 441 giving a curving direction to the curving and insertion driving means 407, an advance directing means 442 giving an advancing direction and a retreat directing means giving a retreating direction. In case the extracted minimum data is smaller than the threshold level, so that the insertable part 402 may be directed at the tip in the direction corresponding to the minimum value, the curvable part 406 will be curved through the curving and insertion driving means 407 by the above mentioned curving directing means 441 and the endoscope 401 will be advanced through the curving and insertion driving means 407 by the above mentioned advance directing means 442. When the extracted minimum value is above the above mentioned threshold level, the endoscope 401 will be retreated through the curving and insertion driving means 407 by the above mentioned retreat directing means 443.

The operation of this embodiment will be explained in the following with reference to FIG. 30.

In the automatic insertion, first, in the step S1 (the word "step" shall be omitted so as to mention S1 hereinafter), the front is illuminated with the illuminating light source. At this time, the automatically inserted lighting window 416 of the visual field mask 16 will be opposed to the image guide 412 on the rear end surface and an image of a visual field narrower than the visual field of the ordinary observation will be formed on the solid state imaging device 418.

In S3, the received light amount of the solid state imaging device 418 is measured by the received light amount measuring means 434. In S3, a determination of whether the scanning has ended or not is made. If NO, in S4, the visual field is converted by the objective lens visual field conversion or the insertable part 402 tip curving operation, the process returns to the above-mentioned S2 and the received light amount of the solid state imaging device 418 is measured. Thus, the predetermined range is scanned and the received light amount in the respective visual field direction is measured.

In S3, the scanning ends and, in S5, the minimum value of the received light amount is extracted by the minimum value extracting means 435.

In S6, the threshold level set by the threshold level setting means 437 is input into the comparing means 436 and, in S7, whether the minimum value is smaller than the threshold level or not is determined by the above mentioned comparing means 436. If YES, in S8, so that the insertable part 402 may be directed at the tip in the direction corresponding to the minimum value of the received light amount, the curvable part 406 is curved through the curving and insertion driving means 407 by the curving directing means 441. In S9, the endoscope 401 is advanced through the curving and insertion driving means 407 by the advance directing means 442 and the process proceeds to S11. In case the minimum value is above the threshold level, in S10, the endoscope 401 is retreated through the curving and insertion driving means 407 by the retreat directing means 443 and the process proceeds to S11.

In S11, based on the information from the automatic insertion operating/stopping switch, it is determined whether the automatic insertion is to be ended or not and, if NO, the process returns to S2 and, if YES, the process ends. For the end of automatic insertion, the visual field mask 416 is rotated by the mask controlling means 432 and the ordinary observing window 416a is opposed to the image guide 412 on the rear end surface. Ordinary observation becomes possible and the manual curving and insertion become possible. The curving and insertion driving means 407 can be not only controlled by the automatic inserting apparatus 430 but also manually operated.

Thus, according to this embodiment, by scanning a visual field narrower than in the ordinary observation and detecting a dark direction, the endoscope inserting direction can be detected, the endoscope can be automatically inserted in the detected inserting direction and therefore it is easy to insert the endoscope.

FIGS. 31 to 32 show the sixth embodiment of the present invention.

In this embodiment, a spectral prism 450 dividing a light bundle into two is provided as opposed to the image guide 412 on the rear end surface. In the light path of the light transmitted through the spectral prism, an ordinary observing mask 451, image forming lens 417b and solid state imaging device 418 are arranged in the order mentioned. In the light path of the light reflected by the above mentioned spectral prism 450, an automatically inserted lighting mask 452, condenser lens 453 and light receiving device 454 are arranged in the order mentioned.

The above mentioned ordinary observing mask 451 is provided with an ordinary observing window 451a of a large visual field as shown in FIG. 32(a) and the above mentioned automatically inserted lighting mask 452 is provided with an automatically inserted lighting window 452a of a small visual field as shown in FIG. 32(b).

The above mentioned solid state imaging device 418 is connected to a signal processing circuit 422 within a control apparatus 420 and the above mentioned light receiving device 454 is connected to an automatic inserting apparatus 430.

In this embodiment, the above mentioned automatic inserting apparatus 430 measures the received light amount of the above mentioned light receiving device 454 instead of the received light amount of the solid state imaging device 418 in the fifth embodiment and controls the endoscope to advance in the direction of the minimum received light amount of this light receiving device 454.

According to this embodiment, even at the time of automatic insertion, the ordinary observation is possible.

This embodiment can be applied also to a fiber scope having no solid state imaging device 418. An eyepiece lens may be provided instead of the image forming lens 417 and solid state imaging device 418 in FIG. 31.

The other formations, operations and effects are the same as in the fifth embodiment.

FIG. 33 shows the seventh embodiment of the present invention.

In this embodiment, within the insertable part 402 of the endoscope 401, an automatically inserted lighting image guide 462 is provided separately from an observing image guide 412. Also, within the operating part 403, as opposed to the above mentioned automatically inserted lighting image guide 462 on the rear end surface, an automatically inserted lighting mask 452, condenser lens 453 and light receiving device 454 are arranged in the order mentioned. The above mentioned light receiving device 454 is connected to an automatic inserting apparatus 430. The same as in the sixth embodiment, the automatic inserting apparatus 430 measures the received light amount of the above mentioned light receiving device 454 and controls the endoscope to advance in the direction of the minimum received light amount of this light receiving device 454.

An eyepiece part 460 is provided at the rear end of the operating part 403 and is provided with an eyepiece lens 461 opposed to the above mentioned observing image guide 412 on the rear end surface. An ordinary observing mask 451 is provided between this eyepiece lens 461 and the rear end surface of the above mentioned image guide 412.

The lens for making the above mentioned automatically inserted lighting image guide 462 form an image may be common with an ordinary observing objective lens 411 or may be separately provided. If the above mentioned automatically inserted lighting image guide 462 is fine enough in diameter, the automatically inserted lighting image guide 462 itself may be made an automatically inserted window without providing the automatically inserted lighting mask 452.

The other formations, operations and effects are the same as in the sixth embodiment.

In the above mentioned fifth to seventh embodiments, the light may be made to directly enter the solid state imaging device 418 and light receiving device 454 through no image guide. Also, the bright and dark information about one picture obtained by scanning a narrow visual field as in the fifth to seventh embodiments may be made an input image of the automatic inserting apparatus 30 in the first to fourth embodiments.

The tip part 410 of the insertable part 402 of the endoscope has been conventionally directed to the center of a tube cavity such as intestines by curving the curvable part while seeing the observed image but this operation has not been easy.

The curvable part 406 is usually covered with a rubber film, is low in slipping, is high in friction with the intestine wall or the like and is low in insertability.

Therefore, an example of an endoscope wherein the tip part 410 of the insertable part 402 can be easily positioned in the center of the tube cavity, friction with the tube cavity can be reduced and insertability is improved is shown in FIGS. 34 to 37.

In the example shown in FIGS. 34 to 36, as shown in FIG. 34, air feeding ports 471 and a sucking port 472 are provided in the tip part 410 of the insertable part 402 of the endoscope 401. As shown in FIG. 35, a plurality of the above mentioned air feeding ports 471 are peripherally provided on the outer periphery of the tip part 410 and the above mentioned sucking port 472 is provided on the tip surface of the tip part 410.

Within a control apparatus 420, there are provided an air feeding source 481, sucking source 482 and control circuit 483 controlling the air feeding source 481 and sucking source 482.

An air feeding pipe line 476 connecting the above mentioned air feeding source 481 with the above mentioned air feeding ports 471 and a sucking pipe line 477 connecting the above mentioned sucking source 482 with the above mentioned sucking port 472 are provided within the insertable part 402, operating part 403 and universal cord 404 of the above mentioned endoscope 401. The formation of the air feeding ports 471, air feeding pipe line 476, sucking port 472 and sucking pipe line 477 are as shown in FIG. 36. A switch 478 operating the above mentioned control circuit 483 is provided in the operating part 403.

In the endoscope of such a formation, in case the tube cavity center is missed or the like, if the switch 478 is pushed, an electric signal will be transmitted from the control circuit 483 to the air feeding source 481 and sucking source 482 so that they may start feeding and sucking air. Air is fed radially from the air feeding ports 471 and is sucked through the sucking port 472. The fed and sucked amount of air are made substantially equal to each other.

By thus feeding air, as shown in FIG. 35, the intestine wall 489 or the like is pushed away and the tip part 410 is positioned substantially in the center of the tube cavity. As substantially the same amount of air is sucked, the organ will not be over-inflated.

By feeding air, the friction with the intestine wall is eliminated and, by pushing the insertable part 402 in the axial direction in this state, the endoscope can be easily inserted.

In the example shown in FIG. 37, air feeding ports 471a feeding air in the radial direction and air feeding ports 471b feeding air obliquely rearward (in the operating part direction) are provided peripherally on the outer periphery of the tip part 410. The other formations are the same as in the example in FIG. 36.

According to this example, by feeding air in the radial direction, the tip part 410 is positioned in the center of the tube cavity and, by feeding air obliquely rearward, a propelling force is obtained and therefore the insertion becomes easier.

As explained above, according to the fifth to seventh embodiments, there are effects that, as a visual field, which is narrower than the ordinary observing visual field, is scanned and the direction of a small received light amount is detected, the endoscope inserting direction can be detected and the insertion of the endoscope can be made easy.

It is apparent that, in this invention, working modes different in a wide range can be formed on the basis of the invention without deviating from the spirit and scope of the invention. This invention is not restricted by its specific working mode except being limited by the appended claims.

What is claimed is:

1. An endoscope insertion controlling apparatus comprising:
   a region extracting means for extracting a plurality of regions corresponding to brightness from an endoscope image by a plurality of brightness threshold levels; and
   a determining means for determining endoscope inserting conditions based on an arrangement of respective regions extracted by said region extracting means.

2. An endoscope insertion controlling apparatus according to claim 1 wherein said determining means includes an operating means for determining center positions of the respective regions extracted by said region extracting means and determines the endoscope inserting conditions based on the arrangement of said center positions of said respective regions determined by said operating means.

3. An endoscope insertion controlling apparatus to claim 2 wherein said determining means considers according at least one of said center positions of said respective regions determined by said operating means as an endoscope inserting direction as of said inserting conditions.

4. An endoscope insertion controlling apparatus according to claim 2 wherein determining means determines an endoscope progress speed of said inserting conditions based on the arrangement of said center positions of said respective regions determined by said operating means.

5. An endoscope insertion controlling apparatus according to claim 2 wherein said determining means includes a displacement means for determining relative displacement of the center positions of said respective regions determined by said operating means and determines an endoscope progress speed of said inserting conditions in response to a magnitude of said displacement.

6. An endoscope insertion controlling apparatus according to claim 1 wherein said region extracting means includes a divaluing means for divaluing said endoscope image with said threshold levels of brightness in order to extract said plurality of regions corresponding to the brightness.

7. An endoscope insertion controlling apparatus according to claim 6 wherein said region extracting means further includes a threshold level setting means for setting said threshold levels based on a histogram of the brightness of said endoscope image.

8. An endoscope insertion controlling apparatus according to claim 7 wherein said threshold level setting means set said threshold levels based on a brightness level of a first peak as seen from a darker side in said histogram of the brightness of said endoscope image.

9. An endoscope insertion controlling apparatus according to claim 1 wherein said determining means includes an operating means for correlation between a shape of the region extracted by said region extracting means and a predetermined shape and determines an endoscope to be retreated when a correlative value determined by said operating means is above a set value.

10. An endoscope insertion controlling apparatus according to claim 1 further comprising a driving means for directing a tip part of an insertable part of an endoscope in a direction determined based on said endoscope inserting conditions determined by said determining means.

11. An endoscope insertion controlling apparatus according to claim 1 further comprising a driving means for advancing or retreating an insertable part of an endoscope based on the endoscope insertable part of an endoscope based on the endoscope inserting conditions determined by said determining means.

12. An endoscope inserting condition determining method comprising the respective steps of:

extracting a plurality of regions corresponding to brightness from an endoscope image by a plurality of brightness threshold levels; and determining endoscope inserting conditions based on an arrangement of the respective regions extracted by said extracting step.

13. An endoscope inserting condition determining method according to claim 12 wherein said determining step is to determine said endoscope inserting conditions based on an arrangement of center positions of the respective regions extracted by said extracting step.

14. An endoscope inserting condition determining method according to claim 13 wherein said determining step is to consider at least one of said center positions of said respective regions as an endoscope inserting direction of said inserting conditions.

15. An endoscope inserting condition determining method according to claim 13 wherein said determining step is to determine an endoscope progress speed of said inserting conditions based on the arrangement of said center positions of said respective regions.

16. An endoscope inserting condition determining method according to claim 13 wherein said determining step is to determine an endoscope progress speed of said inserting conditions in response to a magnitude of a relative displacement of said center positions of said respective regions.

17. An endoscope inserting condition determining method according to claim 12 wherein said extracting step includes divaluing said endoscope image with said threshold levels of brightness in order to extract a plurality of regions corresponding to brightness.

18. An endoscope inserting condition determining method according to claim 17 wherein said extracting step includes setting said threshold levels based on a histogram of the brightness of said endoscope image.

19. An endoscope inserting condition determining method according to claim 18 wherein said extracting step includes setting said threshold levels based on a first peak brightness level as seen from a darker side in said histogram of the brightness of said endoscope image.

20. An endoscope inserting condition determining method according to claim 12 wherein said determining step is to correlate between a shape of the region extracted by said extracting step and a predetermined shape and to determine an endoscope to be retreated when a determined correlative value is above a set value.

21. An endoscope inserting condition determining method according to claim 12 wherein said endoscope image is obtained by an imaging means provided in an endoscope.

22. An endoscope inserting condition determining method according to claim 12 wherein said endoscope image is obtained by a television camera fitted to the eyepiece part of an endoscope with which a naked eye observation is possible.

23. An endoscope apparatus comprising:
an endoscope body having an elongate insertable part including an observing window at a tip and an image forming optical system forming an endoscope image by receiving light incident through said observing window from an object to be imaged;
an imaging means for imaging said endoscope image formed by said image forming optical system;

a region extracting means for extracting a plurality of regions corresponding to brightness from said endoscope image imaged by said imaging means;

a determining means for determining endoscope inserting conditions based on an arrangement of respective regions extracted by said region extracting means;

a first driving means for directing said tip of said insertable part of said endoscope body in a direction determined based on said endoscope inserting conditions determined by said determining means; and a second driving means for advancing or retreating said insertable part of said endoscope based on said endoscope inserting conditions determined by said determining means.

24. An endoscope inserting direction detecting apparatus comprising:

a light receiving means for receiving light from a visual field which is narrower than an ordinary observing visual field of an endoscope;

a scanning means for scanning said visual field of said light receiving means; and a determining means for determining an endoscope inserting direction based on the received light amount by said light receiving means in the respective visual field directions obtained by scanning said visual field of said light receiving means by said scanning means.

* * * * *